(12) United States Patent
Holliday et al.

(10) Patent No.: US 7,947,202 B2
(45) Date of Patent: May 24, 2011

(54) POLYMER-NANOPARTICLE COMPOSITIONS AND METHODS OF MAKING AND USING SAME

(75) Inventors: Bradley J. Holliday, Austin, TX (US);
Alan H. Cowley, Austin, TX (US);
Richard A. Jones, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 253 days.

(21) Appl. No.: 12/194,848

(22) Filed: Aug. 20, 2008

(65) Prior Publication Data
US 2009/0057620 A1 Mar. 5, 2009

Related U.S. Application Data

(60) Provisional application No. 60/965,422, filed on Aug. 20, 2007.

(51) Int. Cl.
*H01B 1/02* (2006.01)
*H01B 1/22* (2006.01)
(52) U.S. Cl. ...... 252/514; 117/84; 136/263; 204/403.01; 257/615; 524/431
(58) Field of Classification Search .......... 252/514; 117/84; 136/263; 204/403.01; 257/615; 524/431
See application file for complete search history.

(56) References Cited

U.S. PATENT DOCUMENTS

| 6,323,309 | B1 | 11/2001 | Swager et al. | 528/380 |
| 7,777,303 | B2 * | 8/2010 | Alivisatos et al. | 257/615 |
| 2003/0114568 | A1 * | 6/2003 | Sato | 524/431 |
| 2003/0226498 | A1 * | 12/2003 | Alivisatos et al. | 117/84 |
| 2004/0124504 | A1 | 7/2004 | Hsu | 257/655 |
| 2005/0133087 | A1 * | 6/2005 | Alivisatos et al. | 136/263 |
| 2007/0029195 | A1 * | 2/2007 | Li et al. | 204/403.01 |

OTHER PUBLICATIONS

Wang et al., "PbS in polymers. From molecules to bulk solids", Dec. 15, 1987, J. Chem Phys., 87 (12), pp. 7315-7322.*
Reddinger et al., "Electroactive, pie-Conjugated Polymers based on Transition Metal-Containing Thiophenes", 1997, Synthetic Metals, 84, pp. 225-226.*
Zotti et al., Conductivity in Redox Modified Conducting Polymers. 2. Enhanced Redox Conductivity in Ferrocene-Substituted Polypyrroles and Polythiophenes, 1995, Chem. Mater., 7, pp. 2309-2315.*
Sun et al., "Photovoltaic Devices Using Blends of Branched CdSe Nanoparticles and Conjugated Polymers", May 2003, Nano-Letters: Amer. Chem. Soc., 3 (7), pp. 961-963.*
Wang et al. PbS in polymers. From molecules to bulk solids, J. Chem. Phys., Dec. 15, 1987, vol. 87, No. 12, p. 7315-7322, p. 7315, col 2 para 2.
International Search Report, PCT/US2008/73732, Dec. 9, 2008.

* cited by examiner

*Primary Examiner* — Mark Kopec
*Assistant Examiner* — Khanh Tuan Nguyen
(74) *Attorney, Agent, or Firm* — Ballard Spahr LLP

(57) ABSTRACT

Disclosed are polymer nanoparticle compositions comprising a film comprising an at least partially electrically conductive oligomer, polymer, or copolymer, and at least one nanoparticle at least partially disposed therein, wherein the at least partially electrically conductive oligomer, polymer, or copolymer is in electrical communication with the nanoparticle. Also disclosed are methods of making and using the polymer nanoparticle compositions.

6 Claims, 16 Drawing Sheets

Mass spec: 750.0150, 639.9       Mass Spec: 751.0146, 231.3

(Ferrocene/ferrocidium redox couple)

(Scheme 2)

(SCHEME 3)

POLYMER-NANOPARTICLE COMPOSITIONS AND METHODS OF MAKING AND USING SAME

CROSS-REFERENCE TO RELATED APPLICATIONS

This application claims the benefit of U.S. Provisional Application No. 60/965,422 entitled "SEEDED GROWTH OF MATERIALS WITHIN CONDUCTIVE POLYMER MATRICES FOR HETEROJUNCTION SOLAR CELLS AND OTHER APPLICATIONS" filed Aug. 20, 2007, the entirety of the disclosure of which is expressly incorporated herein by reference.

BACKGROUND

Electrically conducting polymers are well known for their use in electrical and optical devices due to their ability to transport charge. One drawback to these materials, however, is that electron transport in conducting polymers is much slower than hole transport. In order to transfer electrons more efficiently and to enable exciton generation, preformed nanoparticles have been directly blended with conducting polymers. In theory, such a blend should enable the separation of the exciton at the interface between the two materials, such that the polymer is the hole transporter while the nanoparticles are the electron transporters.

Unfortunately, achieving good communication between the polymer and the nanoparticle using existing methods has proven difficult. It is believed that the difficulty arises due to passivation of the nanoparticle surface by surfactant molecules or oxide coatings. Consequently, devices with these compositions can exhibit a variety of problems. Pertinent examples include solid-state heterojunction solar cells that are challenged by poor efficiency, and room temperature solid-state radiation sensors that do not function optimally. Thus, a need exists for new materials and methods that overcome challenges in the art, a few of which are mentioned above. These needs and other needs are at least partially satisfied by the present invention.

SUMMARY

In accordance with the purpose(s) of the invention, as embodied and broadly described herein, the invention, in various aspects, relates to materials for use in light-emitting devices, energy conversion devices, devices produced therewith, and methods for making same.

In one aspect, the present application provides a polymer-nanoparticle compositions comprising: a film comprising an at least partially electrically conductive oligomer, polymer, or copolymer; and at least one nanoparticle at least partially disposed therein; wherein the at least partially electrically conductive oligomer, polymer, or copolymer is in electrical communication with the nanoparticle. In one specific aspect, the nanoparticle comprises a semiconductor material. In another aspect, the nanoparticle comprises a metal, such as, for example, a transition metal, a platinum group metal, or a combination thereof.

In another aspect, the present application provides methods for producing polymer nanoparticle compositions comprising: providing a film comprising an at least partially electrically conductive oligomer, polymer, or copolymer comprising a plurality of metal complex residues having at least one metal center therein; and growing at least one nanoparticle from the at least one metal center; thereby producing the polymer-nanoparticle composition.

In a still further aspect, disclosed are semiconducting devices comprising: a polymer nanoparticle composition comprising at least one nanoparticle having one or more layers of at least one metal; an at least partially electrically conductive oligomer, polymer, or copolymer; wherein the at least partially electrically conductive oligomer, polymer, or copolymer and the nanoparticle are in electrical communication with each other; and wherein the at least one nanoparticle is produced from at least one metal center in a metal complex residue in the at least partially electrically conductive oligomer, polymer, or copolymer.

In one aspect, disclosed are compounds having a structure represented by a formula:

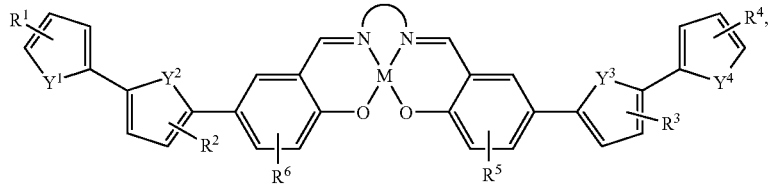

wherein each $Y^1$, $Y^2$, $Y^3$, and $Y^4$ is independently selected from O, S, and NH; wherein M is a metal; wherein each $R^1$, $R^2$, $R^3$, and $R^4$ independently comprises 3 substituents independently selected from hydrogen and optionally substituted organic residue comprising from 1 to 12 carbons; wherein each $R^5$ and $R^6$ independently comprises 3 substituents independently selected from hydrogen and optionally substituted organic residue comprising from 1 to 12 carbons; wherein the general structural residue

represents a ligand selected from optionally substituted heteroalkyl, optionally substituted heterocycloalkyl, and optionally substituted heteroaryl; or an oligomer, polymer, or nanoparticle produced therefrom. In one aspect, the metal comprises Cd, Pb, Ga, or a combination thereof. In another aspect, the metal comprises a transition metal, such as for example, Co; an inert metal, such as, for example, gold; a platinum group metal, such as, for example, platinum, palladium, ruthenium; or a combination thereof.

In a further aspect, disclosed are oligomers, polymers, or copolymers comprising a residue represented by a formula:

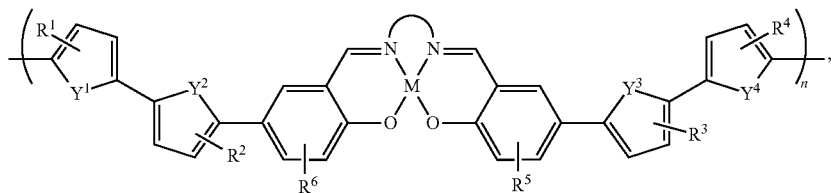

wherein n is an integer from 1 to 100,000; wherein each $Y^1$, $Y^2$, $Y^3$, and $Y^4$ is independently selected from O, S, and NH; wherein M is a metal; wherein each $R^1$ and $R^4$ independently comprises 2 substituents independently selected from hydrogen and optionally substituted organic residue comprising from 1 to 12 carbons; wherein each $R^2$ and $R^3$ independently comprises 3 substituents independently selected from hydrogen and optionally substituted organic residue comprising from 1 to 12 carbons; wherein each $R^5$ and $R^6$ independently comprises from 1 to 3 substituents independently selected from hydrogen and optionally substituted organic residue comprising from 1 to 12 carbons; wherein the general structural residue

represents a ligand selected from optionally substituted heteroalkyl, optionally substituted heterocycloalkyl, and optionally substituted heteroaryl; or a nanoparticle produced therefrom. In another aspect, the metal comprises a transition metal, such as for example, Co; an inert metal, such as, for example, gold; a platinum group metal, such as, for example, platinum, palladium, ruthenium; or a combination thereof.

While aspects of the present disclosure can be described and claimed in a particular statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
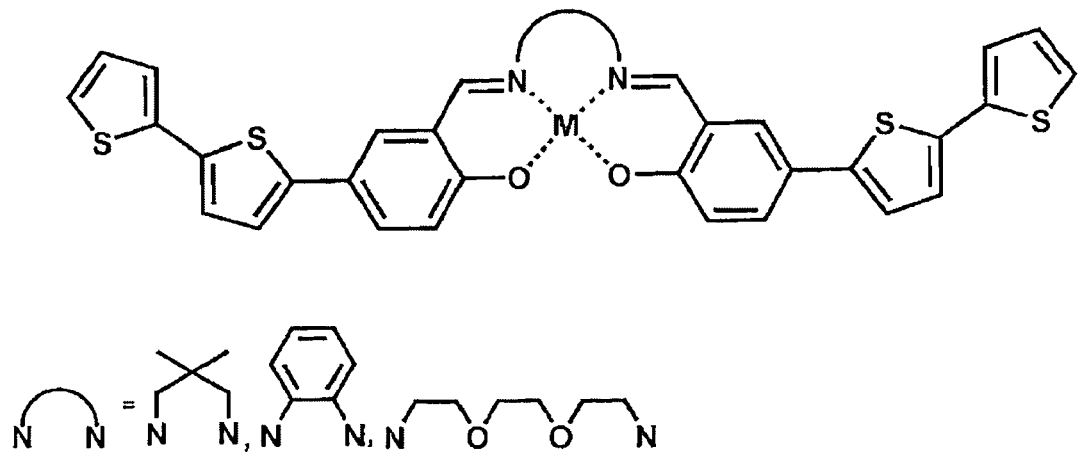
FIG. 1 is an illustration of the chemical structure of one particular, non-limiting embodiment of a class of monomers made in accordance with the teachings herein which have a metal center and a conducting polymer precursor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates.

A. Definitions

As used in the specification and the appended claims, the singular forms "a," "an" and "the" include plural referents unless the context clearly dictates otherwise. Thus, for example, reference to "a metal complex residue," "a polymer," or "a nanoparticle" includes mixtures of two or more such metal complex residues, polymers, or nanoparticles, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, a bithiopene residue in a polythiophene refers to one or more bithiophene units in the polythiophene, regardless of whether bithiophene was used to prepare the polythiophene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. The term "optionally substituted," means that the compound, atom, or residue can or cannot be substituted, as defined herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, 1 to 20 carbons, 1 to 18 carbons, 1 to 16 carbons, 1 to 14 carbons, 1 to 10 carbons, 1 to 8 carbons, 1 to 6 carbons, 1 to 4 carbons, 1 to 3 carbons, or 1 to 2 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

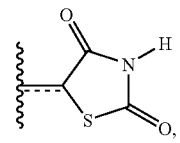

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a cation for anionic inorganic radicals such as a sulfate, phosphate, or like anionic inorganic radical.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

If a disclosed chemical species is said to be "conjugated," it is meant that the chemical species has at least two conjugated π bonds. For example, if a chemical species has alternating π and sigma bonds, that chemical species is conjugated. In one aspect, conjugation refers to at least partial electron (e.g., π electron) delocalization, although conjugation does not guarantee electron delocalization. An example of a conjugated chemical species is an aryl group, as discussed herein.

As used herein, the term "copolymer" refers to a polymer formed from two or more monomers, polymers, or a combination thereof. By way of example and without limitation, a copolymer can be an alternating copolymer, a random copolymer, a block copolymer, a graft copolymer, a terpolymer, or a combination thereof.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

B. Polymer-Nanoparticle Compositions

In one aspect, a disclosed polymer-nanoparticle composition comprises: a film comprising an at least partially electrically conductive oligomer, polymer, or copolymer; and at least one nanoparticle at least partially disposed therein; wherein the at least partially electrically conductive oligomer, polymer, or copolymer is in electrical communication with the nanoparticle. In one specific aspect, the nanoparticle comprises a semiconductor material. In another specific aspect, the nanoparticle comprises a transition metal, an inert metal, a catalytic metal, a platinum group metal, or a combination thereof.

In one aspect, the metal comprises a semiconductor material. In a specific aspect, the metal comprises Cd, Pb, Ga, or a combination thereof. In another aspect, a semiconductor material comprises Cd, Pb, Ga, a sulfide or selenide thereof, or a combination thereof, such as, for example, cadmium sulfide, cadmium selenide, gallium sulfide, gallium selenide, copper indium sulfide, copper indium selenide.

In another aspect, the metal comprises a transition metal, such as, for example, Co, an alloy thereof, a mixture of transition metals, and/or a mixture of a transition metal and another metal.

In yet another aspect, the metal comprises an inert metal, such as, for example, gold, an alloy thereof, a mixture of inert metals, and/or a mixture of an inert metal and another metal.

In still another aspect, the metal comprises a platinum group metal, such as, for example, platinum, palladium, ruthenium, an alloy thereof, a mixture of platinum group metals, and/or a mixture of a platinum group metal and another metal.

As used herein, when two components are in "electrical communication," it is intended that those two components can engage in charge transfer, capture, or charge delocalization amongst each other. For example, when a disclosed at least partially electrically conductive polymer film comprises nanoparticles disposed therein, energy (e.g., current) can flow from the nanoparticle to the polymer and vice versa.

In a further aspect, a polymer can be bonded to a nanoparticle in a polymer-nanoparticle composition. For example, a nanoparticle, such as, for example, a semiconducting nanoparticle, can be bonded to at least one metal center present in a metal complex residue in the at least partially electrically conductive oligomer, polymer, or copolymer by means of an —S— bond, or another suitable bond. As will be apparent from the foregoing discussion, a polymer film comprising a metal complex can be exposed to hydrogen sulfide ($H_2S$), thereby forming thiol ligands on the metal center (i.e., M-SH). Subsequently, for example, a solution of $M^{n+}$ can be added to the film, thereby forming an M-S-M bond. While not wishing to be bound by theory, such a bond can be covalent (i.e., M-S-M), or ionic.

In a still further aspect, the at least one semiconducting nanoparticle can be grown from at least one metal center in a metal complex residue in the at least partially electrically conductive oligomer, polymer, or copolymer. In a further aspect, electrical communication between a nanoparticle and an oligomer, polymer, or copolymer can be achieved by growing the nanoparticle from a metallic seed point within the oligomer, polymer, or copolymer. Thus, for example, a polymer can synthesized with metal sites built into the backbone of the polymer. The metal sites or atoms are then used to seed the growth of individual nanoparticles. This approach can, in various aspects, electrically connect the two materials together so as to at least partially eliminate interferences to electron or hole transfer (i.e., one material is literally grown around the other). Thus, in one aspect, a polymer-nanoparticle composition comprising a nanoparticle grown from a polymer seed point therein can provide interfacial interactions desired for exciton dissociation and transport.

It should also be appreciated that in addition to the improvements in charge transfer efficiency, this approach can also permit the spacing of the seed or growth sites to be readily manipulated so that they may be spaced at desired intervals which optimize density and homogeneity in the resulting polymer-nanoparticle composition. Thus, for example, in one embodiment of a methodology in accordance with the teachings herein, a seed point may be diluted out with other conductive polymers (e.g., alternating copolymers) that do not contain a metal seed point, thus allowing control of the number of nanoparticles formed and the distance therebetween. In further aspects, a similar effect may be achieved by tailoring the monomer so as to control the conductive polymer portion that is connected to it.

In another aspect, XPS analyses were performed on prepared exemplary films comprising a semiconductor nanoparticle to characterize the concentrations of cadmium and sulfur and the relative concentrations of the two. These results indicated that the stock solution used for the electrochemical deposition accurately reflects what is actually deposited on the film. Thus, in one aspect, a film can comprise the same or substantially the same composition as that of a stock solution.

It is understood that the polymer-nanoparticle compositions can be used in combination with the disclosed compounds, oligomers, polymers, copolymers, nanoparticles, methods, and devices.

C. Polymers

In one aspect, the polymer can be an at least partially electrically conductive polymer. It should be appreciated that, in various aspects, the conducting polymer is conducive to being p-doped, and as such is suitable for use with one or more disclosed embodiments.

Both the term "polymer" and "oligomer" are intended to refer to a macromolecule with repeating units of a structural residue, as discussed herein. Generally, however, an oligomer has a smaller number of repeating units than does a polymer. However, depending on the polydispersity of the polymer, in one aspect, the presence of a polymer ensures that at least one oligomer is present. However, the presence of an oligomer does not necessarily guarantee the presence of a polymer. An example of an oligomer is a dimer, trimer, tetramer, pentamer, and the like. An example of a polymer is a 20 mer, 30 mer, 40 mer, 50 mer, 60 mer, 100 mer, 1000 mer, or even a 100,000 mer. Due to the overlapping nature of polymers and oligomers, the two terms can, in some aspects, be used interchangeably.

In one aspect, an oligomer, polymer, or copolymer can be formed from a disclosed compound. A disclosed compound can be represented as A1-G-A2 wherein A1 and A2 are polymerizable moieties, and wherein G is a metal complex. G can be a complex or cluster. In one aspect, the compound can be conjugated.

In a further aspect, a disclosed compound can have a structure represented by a formula:

pendently selected from hydrogen and optionally substituted organic residue comprising from 1 to 12 carbons; wherein the general structural residue

represents a ligand selected from optionally substituted heteroalkyl, optionally substituted heterocycloalkyl, and optionally substituted heteroaryl.

In one aspect,

is present in a disclosed compound, or oligomer, polymer, or nanoparticle produced therefrom as:

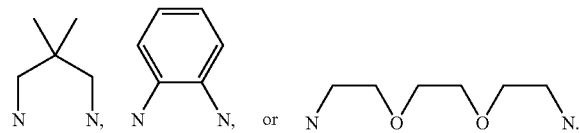

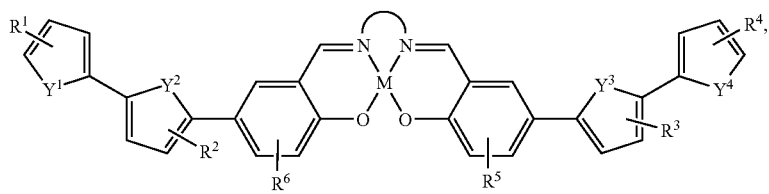

wherein each $Y^1$, $Y^2$, $Y^3$, and $Y^4$ is independently selected from O, S, and NH; wherein M is a metal; wherein each $R^1$, $R^2$, $R^3$, and $R^4$ independently comprises 3 substituents independently selected from hydrogen and optionally substituted organic residue comprising from 1 to 12 carbons; wherein each $R^5$ and $R^6$ independently comprises 3 substituents inde- In a further aspect, a compound can have a structure represented by a formula:

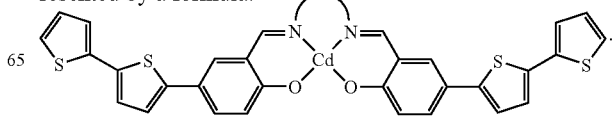

For example, the compound can be present as:

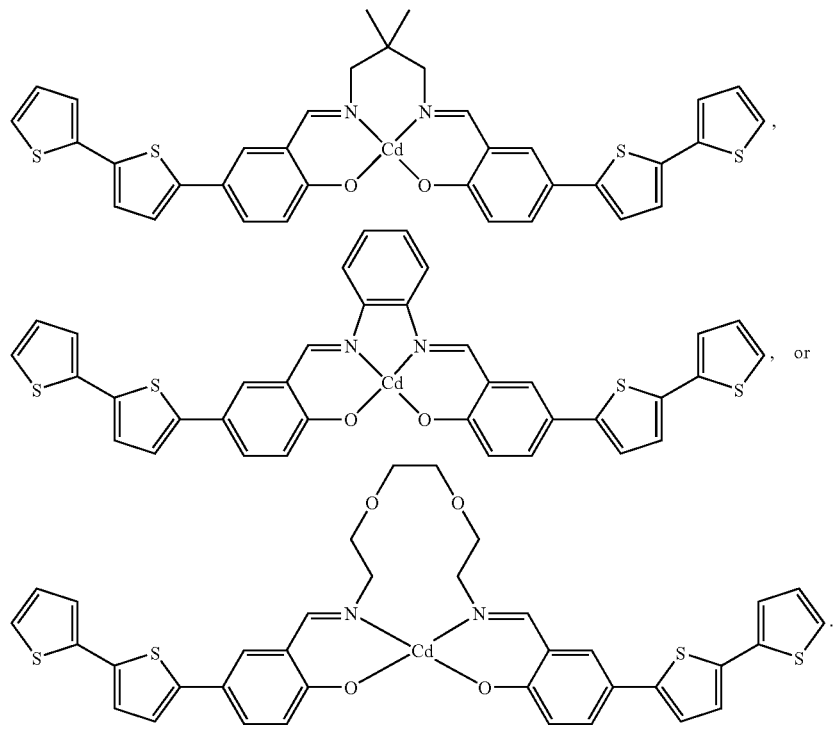

In one aspect, an exemplary polymer can have a structure represented by a formula:

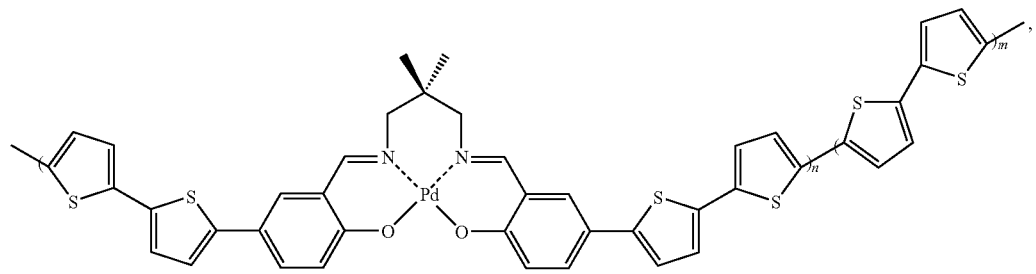

wherein n and m are independently selected integers from 1 to 100,000. Such a polymer can be used, for example, as a catalyst for an oxidation reduction reaction. It will be apparent that the above mentioned Pd based polymer and like polymers can, in some aspects, function better as a catalyst during a given reaction, such as, for example, an oxygen reduction reaction.

Figure 2:
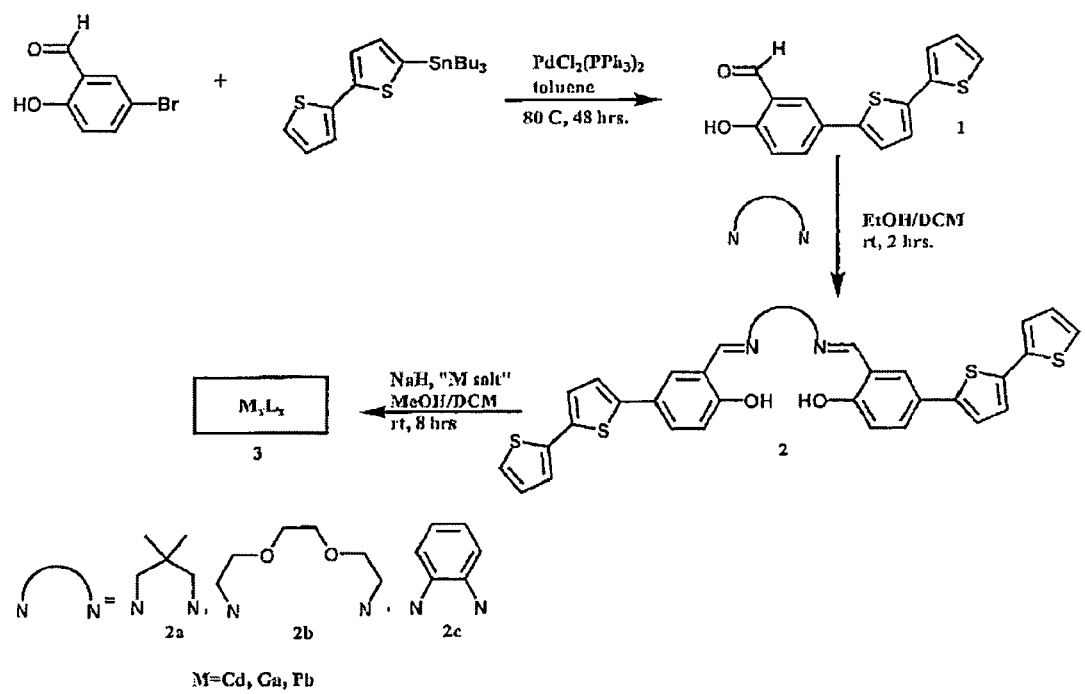
FIG. 2 is an illustration of a synthetic route which may be utilized to synthesize the monomers of FIG. 1.

With reference to FIG. 1, an exemplary class of compounds is illustrated. The synthesis of this class of monomers is illustrated in FIG. 2. This particular class of monomeric species features a metal ligand which is capable of binding to a large variety of metals, and which is flanked on each side with bithiophene moieties, the latter of which are extensively conjugated and form the polymerizable portion of the ligand.

It is to be noted, of course, that various other monomers which are capable of forming conductive polymers could be substituted for the bithiophene moieties. This choice of monomers provides one means by which the material may be synthetically tailored to change the bandgap of the polymer. The material may also be tailored through the choice of polymer backbone (indicated in FIG. 1 by the U-shaped curve) and the choice of metal.

Figure 3:
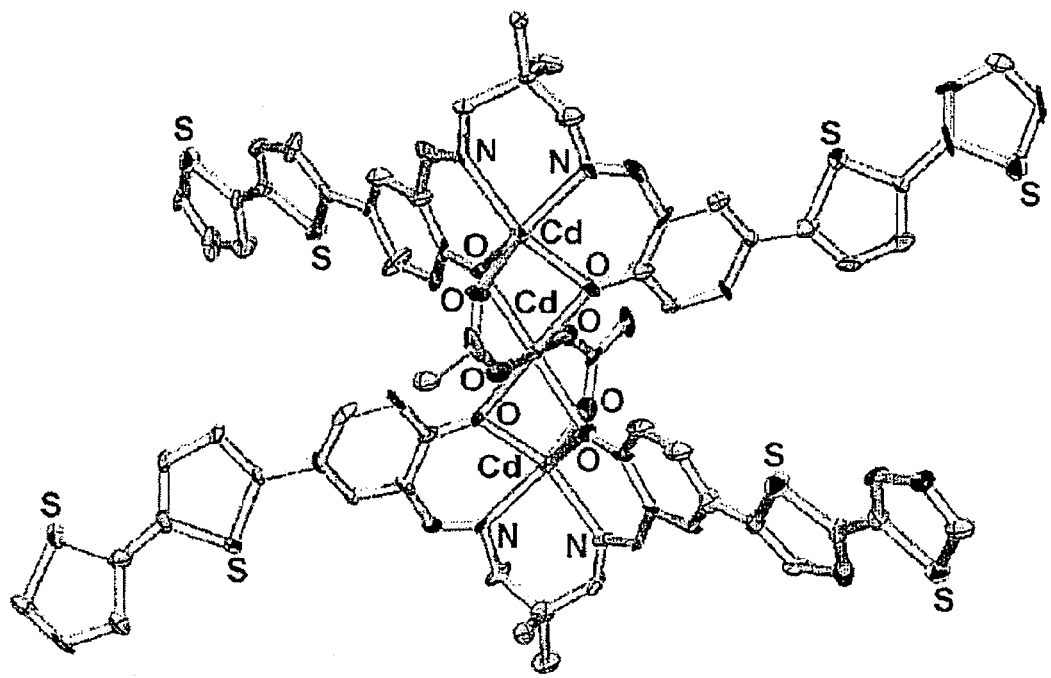
FIG. 3 is an illustration of the crystal structure of one particular species in the class of monomers (a tri-nuclear monomer) depicted in FIG. 1.
Figure 4:
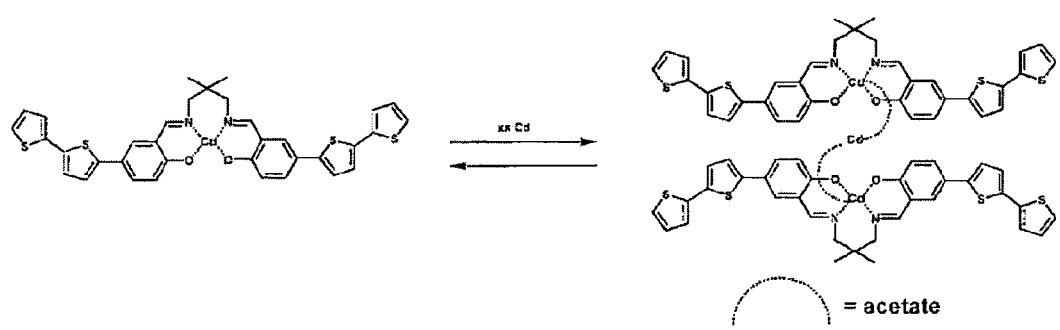
FIG. 4 is an illustration of the equilibrium existing between a tri-nuclear species and a mono-nuclear species in a cadmium monomer made in accordance with the teachings herein, wherein the center cadmium in the compound is held in place by two residual acetates from the cadmium acetate starting material.

FIG. 3 illustrates the crystal structure of one of the exemplary monomeric species depicted in FIG. 1. As shown, the material depicted has three cadmium atoms which can be incorporated into two polymerizable ligands, and hence have the form of a small tri-nuclear cluster compound. The center cadmium in the compound can be held in place by two residual acetates from the starting material (cadmium acetate). This compound has been found to exist in equilibrium between the tri-nuclear species and a mono-nuclear species, as indicated in FIG. 4.

It is understood that a one or more structural features of a disclosed compound can be present in an oligomer, polymer, or copolymer produced therefrom. For example, a metal complex, when present in a disclosed compound, can be present in a polymer produced from the disclosed compound.

In one aspect, an oligomer, polymer, or copolymer comprises a residue represented by a formula:

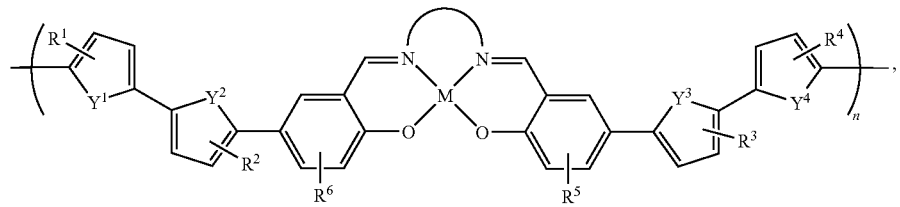

wherein n is an integer from 1 to 100,000; wherein each of $Y^1$, $Y^2$, $Y^3$, and $Y^4$ is independently selected from O, S, and NH; wherein M is a metal; wherein each $R^1$ and $R^4$ independently comprises 2 substituents independently selected from hydrogen and optionally substituted organic residue comprising from 1 to 12 carbons; wherein each $R^2$ and $R^3$ independently comprises 3 substituents independently selected from hydrogen and optionally substituted organic residue comprising from 1 to 12 carbons; wherein each $R^5$ and $R^6$ independently comprises from 1 to 3 substituents independently selected from hydrogen and optionally substituted organic residue comprising from 1 to 12 carbons; wherein the general structural residue

represents a ligand selected from optionally substituted heteroalkyl, optionally substituted heterocycloalkyl, and optionally substituted heteroaryl. In one aspect, M is any metal suitable for use with the present invention. In another aspect, M is a metal selected from Cd, Pb, Cu, and Ga. In other aspects, M is a metal comprising a semiconductor material, a transition metal, an inert metal, a catalytic metal, a platinum group metal, an alloy thereof, or a combination thereof, as otherwise disclosed for the various aspects of the present invention.

In one aspect, a copolymer can comprise a residue represented by a formula:

In one aspect, n, m, or both can be within the range of about 10 to about 100,000. For example, n or m can be within the range of about 100 to about 10,000, within the range of about 1,000 to about 10,000, within the range of about 2 to about 10, and even within the range of about 5 to about 20.

In one aspect, a disclosed oligomer, polymer, or copolymer can be formed into a film. In a further aspect, a disclosed compound can be polymerized to provide a film comprising a disclosed oligomer, polymer, or copolymer.

In one aspect, a film can be a polymer matrix. For example, if a polymer film will be used to grow nanoparticles at least partially therein, then in one aspect, the film can be at least partially permeable, such that solvent comprising a nanoparticle precursor (e.g., a metal salt) can penetrate the film.

It is contemplated that a film can be any thickness suitable for use with the embodiments disclosed herein. A polymer film can have a thickness in the nanometer regime. For example, a film can have a thickness of from about 1 nm to about 1000 nm, from about 10 nm to about 1000 nm, from about 100 nm to about 1000 nm, from about 1 nm to about 500 nm, from about 10 nm to about 500 nm, from about 50 nm to about 500 nm, from about 50 nm to about 200 nm, from about 50 nm to about 250 nm, from about 50 nm to about 300 nm, or even from about 200 nm to about 300 nm.

Alternatively, or in addition to, a film can have a thickness in the micrometer regime. For example, a film can have a thickness of from about 1 μm to about 1000 μm, from about 10 μm to about 1000 μm, from about 100 μm to about 1000 μm, from about 1 μm to about 500 μm, from about 10 μm to about 500 μm, from about 50 μm to about 500 μm, from about 50 μm to about 200 μm, from about 50 μm to about 250 μm, from about 50 μm to about 300 μm, or even from

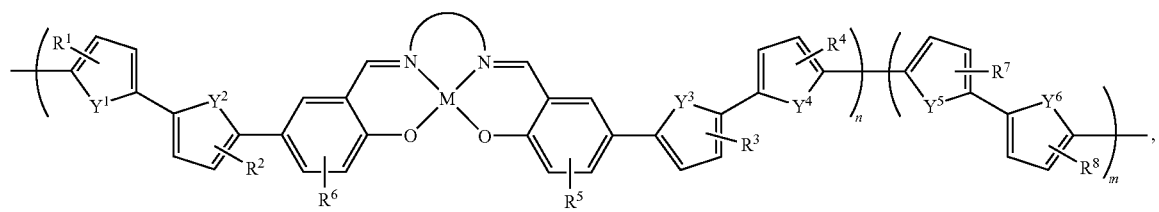

wherein m is an integer from 1 to 100,000; wherein each $Y^5$ and $Y^6$ is independently selected from O, S, and NH; wherein each $R^7$ and $R^8$ independently comprises 2 substituents independently selected from hydrogen and optionally substituted organic residue comprising from 1 to 12 carbons.

In one aspect, M can be present as part of a complex, cluster, or a combination thereof. For example, M can be present as part of a trinuclear cluster as shown in the ORTEP drawing of the crystal structure shown in FIG. 3.

about 200 μm to about 300 μm. In other aspects, a film can have a thickness greater than or less than any specifically recited value, and the present invention is not intended to be limited to any particular film thickness. In yet other aspects, the thickness of a film or any portion thereof can remain constant or vary along the surface of the film.

Film thickness can be determined by routine methods known in art. For example, film thickness can be determined by spectroscopic ellipsometry, atomic force microscopy (AFM), transmission electron microscopy (TEM), among other methods.

Figure 5:
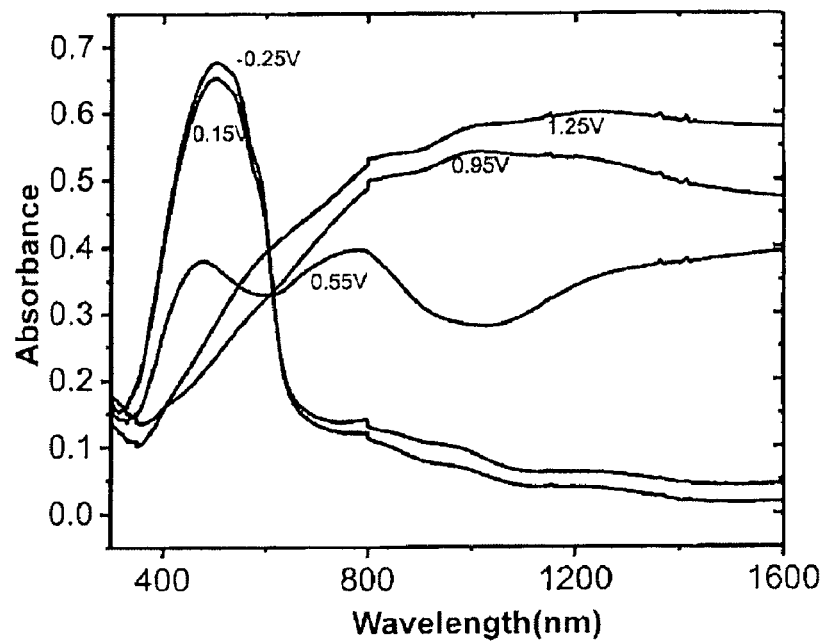
FIG. 5 depicts the UV visible absorption spectra of the polymer of FIG. 7, taken at the points noted in the cyclic voltammogram of FIG. 6.
Figure 6:
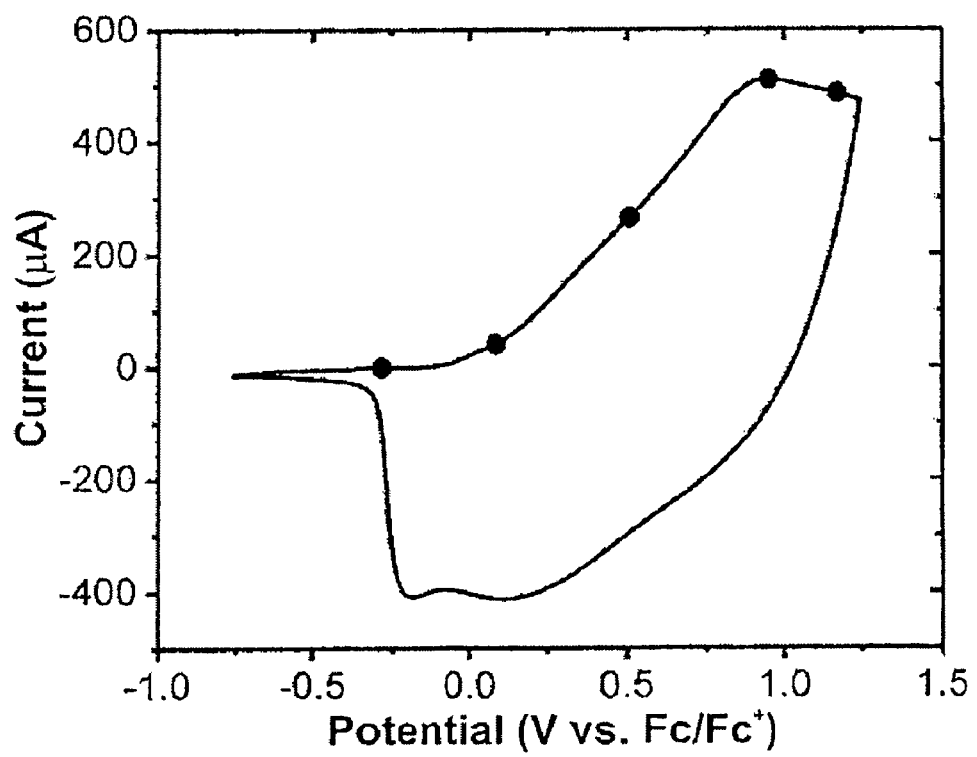
FIG. 6 is a cyclic voltammogram of the polymer shown in FIG. 7.
Figure 7:
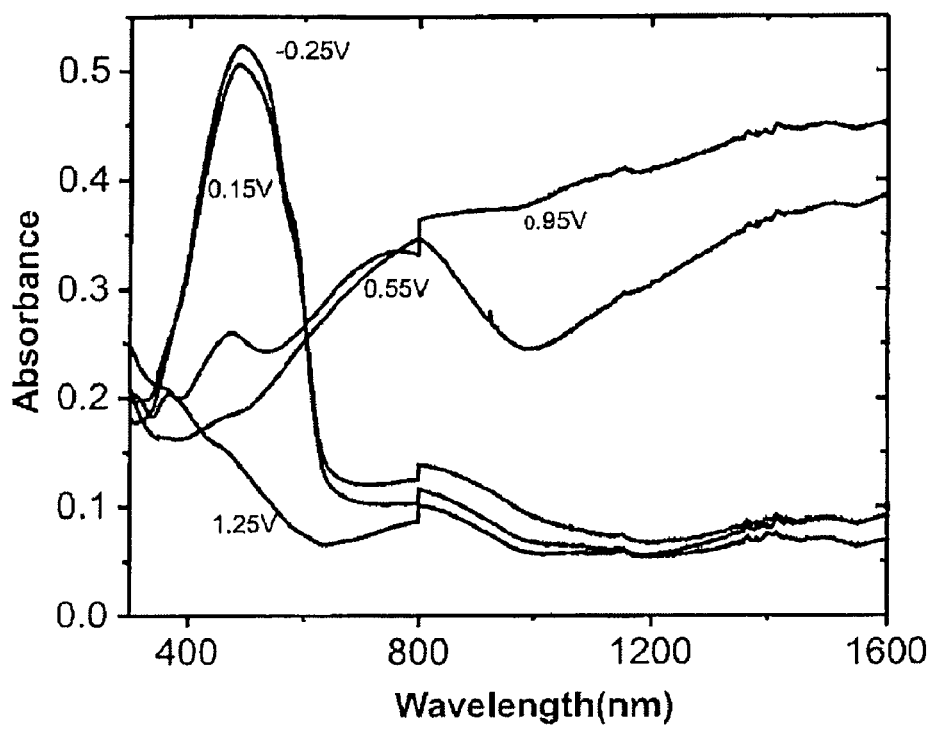
FIG. 7 depicts the UV visible absorption spectra of the copolymer of FIG. 31, taken at the points noted in the cyclic voltammogram of FIG. 8.
Figure 8:
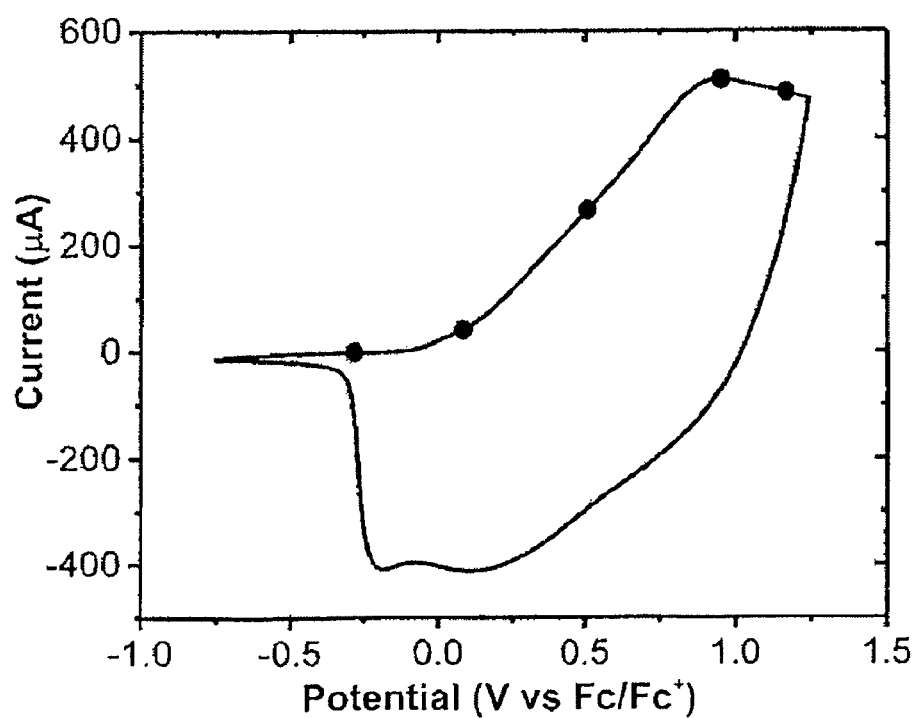
FIG. 8 is a cyclic voltammogram of the polymer shown in FIG. 31.

Referring now to FIGS. 5-6 and 7-8, a disclosed film can be characterized spectroscopically, for example by using electrochemistry and UV-visible (UV-vis) spectroscopy. FIGS. 5-6, for example, illustrate data collected on a film prepared in accordance with the various aspects of the present invention before nanoparticles were grown. In contrast, FIGS. 7-8 illustrate data collected on the film after nanoparticles have been grown.

FIGS. 6 and 8 are exemplary cyclic voltammograms of two films. Each of the points on the voltammograms is a point at which the voltammogram was stopped and held in place while a UV-visible spectrum, such as obtained in FIGS. 5 and 7, was obtained from the film.

As seen in FIGS. 5-6 and 7-8, as potentials are being reduced, there is a strong adsorption in the film at about 425 nm. At highly oxidized states, on the other hand (that is, at about 1-1.25 volts), the conducting polymer can be doped and conducting, thus resulting in a large UV-visible adsorption peak that covers most of the UV-visible spectrum and even extends into the near infrared region. It will apparent that the absorption peak extends above 1600 nm; however, the spectrum is cut off at this point. The specific oxidation state, potential, and/or resulting absorption peak position can vary depending upon, for example, the specific materials, structure, and devices utilized. One of skill in the art could readily determine appropriate conditions, compounds of the present invention, and configurations to obtain a film having desired properties, and the present invention is not limited to any particular component, conditions, or parameters.

In one aspect, a film can be used to grow nanoparticles therein. For example, a polymer film comprising a plurality of metal complex residues having one or more metal centers therein can be used to generate nanoparticles. A nanoparticle, when present in a disclosed film, can be at least partially disposed in the film. For example, a nanoparticle can be completely disposed in the film. A nanoparticle can also partially disposed in the film, such that at least a portion of the nanoparticle is extruding out of the film.

It is understood that the compounds, oligomers, polymers, and copolymers can be used in combination with the disclosed polymer-nanoparticle compositions, methods, and devices.

D. Nanoparticles

Any nanoparticle compatible with a disclosed embodiment can be used. In one aspect, the nanoparticle is a semiconducting nanoparticle. A semiconducting nanoparticle is a nanoparticle that can exhibit electrical conductivity between a conductor and an insulator. Any suitable semiconducting material can be utilized in the various aspects of the present invention. A non-limiting example of a semiconducting nanoparticle is a quantum dot, whose excitons are confined in all three spatial dimensions. As a result, quantum dots have properties that are between those of bulk semiconductors and those of discrete molecules.

In another aspect, the nanoparticle can comprise a metal, such as, for example, a transition metal, an inert metal, a catalytic metal, a platinum group metal, an alloy thereof, and/or a combination thereof. In a specific aspect, the nanoparticle can comprise a transition metal, such as, for example, cobalt, or an alloy thereof. In another specific aspect, the nanoparticle can comprise an inert metal, such as, for example, gold, or an alloy thereof. In yet another aspect, the nanoparticle can comprise a catalytic metal such as, for example, platinum, or an alloy thereof. In still another aspect, the nanoparticle can comprise a platinum group metal, such as, for example, platinum, palladium, ruthenium, an alloy and/or a combination thereof. In yet other aspects, the nanoparticle can comprise a combination of any of the recited metals, for example, semiconducting materials, transition metals, inert metals, catalytic metals, platinum group metals, alloys or combinations thereof.

In one aspect, the nanoparticle has a diameter, which can also be referred to as a particle size. It should be understood that particle sizes can vary and can be distributional properties. When the nanoparticle is provided as a collection of nanoparticles, the diameter refers to the average diameter of the nanoparticles in the collection. While referring to the particle size as a diameter, it is understood that the particles can be spherical, approximately spherical, or nonspherical. In nonspherical cases, the diameter typically refers to the diameter of a sphere having the same hydrodynamic volume of the particle.

In one aspect, the nanoparticle can have an average particle size in the nanoscale regime (e.g. having at least one dimension of a size of from about 1 nm to about 1,000 nm, for example, from about 1 nm to about 500 nm, from about 1 nm to about 250 nm, from about 1 nm to about 100 nm, from about 1 nm to about 80 nm, from about 1 nm to about 70 nm, from about 1 nm to about 60 nm, from about 1 nm to about 50 nm, from about 1 nm to about 40 nm, from about 1 nm to about 30 nm, from about 1 nm to about 20 nm, from about 1 nm to about 10 nm, from about 1 nm to about 8 nm, from about 1 nm to about 6 nm, from about 1 nm to about 5 nm, from about 1 nm to about 4 nm, from about 1 nm to about 3 nm, or even from about 1 nm to about 2 nm. In another aspect, the nanoparticle can have an average particle size less than or greater than any of the recited values, depending upon, for example, the intended application, and the present disclosure is not intended to be limited to any particle nanoparticle particle size.

In a further aspect, the diameter of the nanoparticle can be controlled by the method of preparation. For example, by controlling the temperature of the preparation mixture, growth kinetics can be favored relative to nucleation (also referred to as nanoparticle formation or initiation) kinetics. Consequently, a collection of nanoparticles can be provided with an unusually narrow particle size distribution. In a further aspect, by further controlling the temperature of the preparation mixture, growth kinetics can be disfavored. Consequently, the size of the nanoparticle or collection of nanoparticles can be limited to a particular size or diameter.

In a further aspect, layered growth of the nanoparticle can be carried out. For example, a film comprising a polymer having a metal center therein can provide a seed point for nanoparticle growth. In one aspect, a binding agent (e.g., $H_2S$) can optionally be added to the film, followed by a metal salt. This process can be repeated to provide, for example, a layer of metal having a sulfide bond therebetween. In such a case, the size of a produced nanoparticle can vary depending on the number of iterations of such a process.

Figure 9:
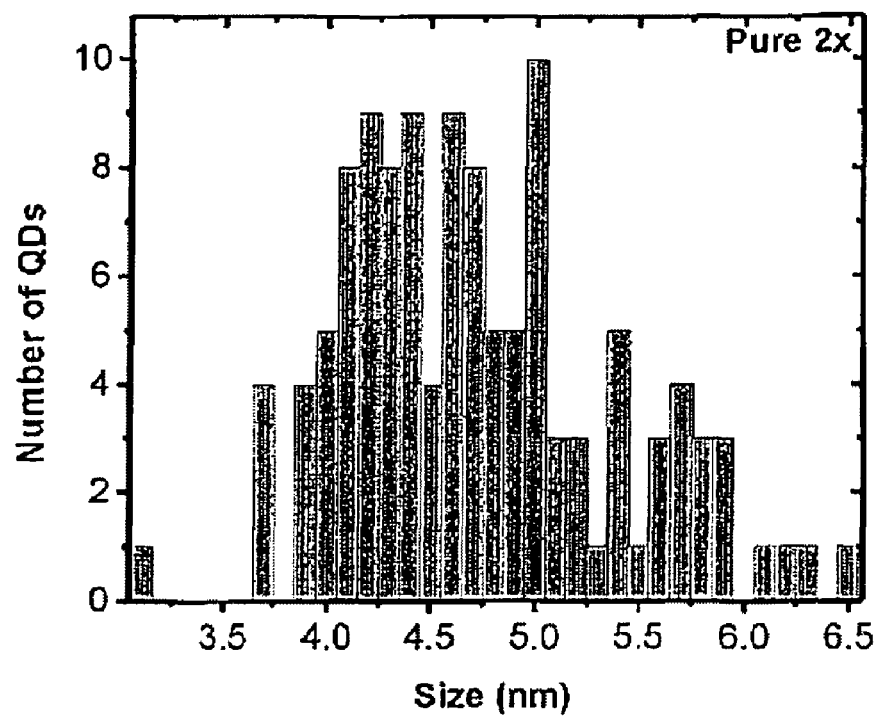
FIG. 9 is a graph of the size distribution of nanoparticles formed after two cycles of the process depicted in FIG. 22.

The chart of FIG. 9 shows the size distribution of exemplary nanoparticles. The exemplary data illustrated in FIG. 9 is based on pure (undiluted) cadmium-containing monomer after two cycles of the Cd/S growth process, as discussed above. In this example, the average size of the nanoparticles after two cycles is about 4.5 nm in diameter.

Figure 10:
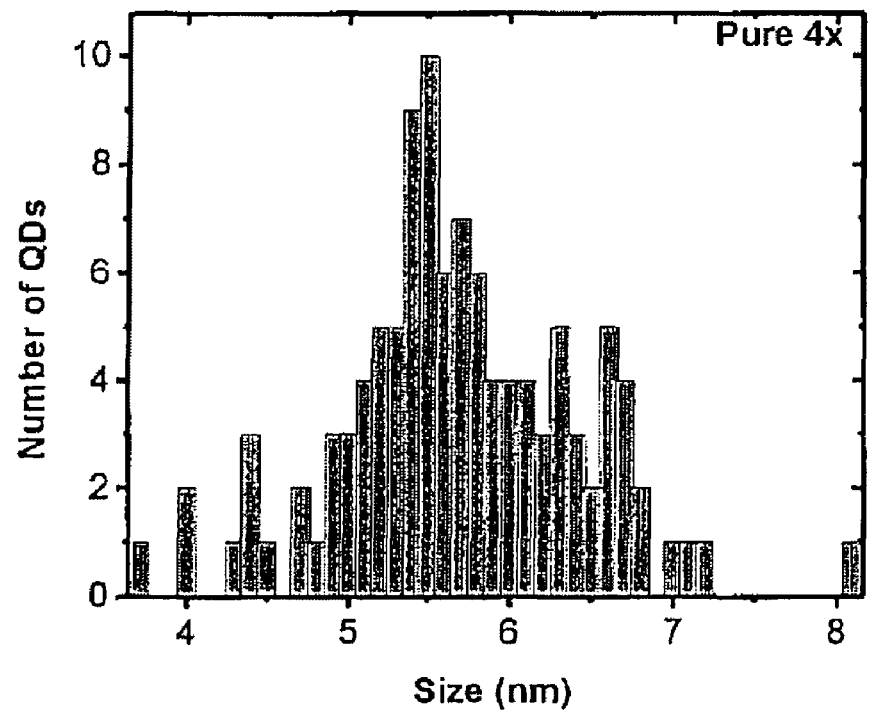
FIG. 10 is a graph of the size distribution of nanoparticles formed after four cycles of the process depicted in FIG. 22.

By comparison, the chart of FIG. 10 illustrates exemplary results obtained after four cycles of the Cd/S growth process. In this example, nanoparticles continue to grow (to an average size of about 5.5 nm after 4 cycles of the Cd/S growth process), thereby indicating that the size of the nanoparticles can be readily controlled by the number of Cd/S cycles. In this example, the distribution of nanoparticle sizes becomes smaller as the number of cycles increases. Thus, the average particle size and particle size distribution can vary and can be at least partially tailored by, for example, the iterative growth process described herein.

It will be apparent that semiconductor nanoparticles, when present in a disclosed device, can function as the absorbing material and the electron conducting material, due to their good electron conducting properties their unique absorption properties. It is known, for example, that the size distribution of a nanoparticle can be manipulated to enable the nanoparticle to capture essentially the entire region of the spectrum of interest.

In a further aspect, the nanoparticle can have a diameter capable of absorbing energy from a first electromagnetic region and capable of emitting light in a second electromagnetic region. In one specific aspect, the nanoparticle can have a diameter of less than about 5.0 nm. In another specific aspect, the nanoparticle can have a second electromagnetic region comprising an at least about 50 nm wide band of wavelengths. In one aspect, the nanoparticle can exhibit a broad band adsorption over the visible region of the electromagnetic spectrum. In a further aspect, the nanoparticle can exhibit a broad band adsorption over the near infrared region of the electromagnetic spectrum.

In one aspect, the nanoparticle of the invention can further comprise an inorganic element. The inorganic nanoparticle can comprise, for example, cadmium selenide, cadmium sulfide, cadmium telluride, zinc sulfide, zinc selenide, zinc telluride, magnesium sulfide, magnesium selenide, magnesium telluride, zinc sulfide, magnesium sulfide, or a mixture thereof. In a further aspect, inorganic nanoparticle can comprise, for example, cadmium oxide, magnesium oxide, zinc oxide, aluminum oxide, titanium dioxide, cadmium sulfoselenide, or cadmium selenium oxide.

In a further aspect, the nanoparticle of the invention can comprise one or more of the following semiconductors: CdS, CdSe, CdTe, $Ga_2S_3$, $Ga_2Se_3$, $Ga_2Te_3$, CuGaS2, $CuGaSe_2$ PbS, PbSe, $CuInS_2$, $CuInSe_2$, or a combination thereof.

In another aspect, the nanoparticle can be suitable for use in an energy conversion device, such as, for example, a fuel cell. In various aspects, the nanoparticle can be suitable for use as a catalyst, for example, for oxygen reduction, in such a device.

It is understood that the nanoparticles can be used in combination with the disclosed compounds, oligomers, polymers, copolymers polymer-nanoparticle compositions, methods, and devices. For example, a nanoparticle can be grown from a disclosed copolymer to provide a disclosed polymer-nanoparticle composition.

E. Devices Comprising Polymer-Nanoparticle Compositions

In one aspect, a polymer-nanoparticle composition can be present in a device. It is contemplated that the disclosed materials can be suitable for use with a variety of electrical and optical devices, such as, for example, photoconductors, photovoltaic cells, electronic materials, luminescent devices, oxygen reduction electrodes, fuel cells, and sensors.

In one aspect, a semiconducting device comprises a polymer nanoparticle composition comprising at least one semiconducting nanoparticle having one or more layers of at least one metal; an at least partially electrically conductive oligomer, polymer, or copolymer; wherein the at least partially electrically conductive oligomer, polymer, or copolymer and the semiconducting nanoparticle are in electrical communication with each other. In another aspect, the at least one semiconducting nanoparticle is produced from at least one metal center in a metal complex residue in the at least partially electrically conductive oligomer, polymer, or copolymer. For example, the polymer nanoparticle composition can be present in a photovoltaic cell, a photoconductor, or at least one layer of a light emitting diode, or other related device. The polymer nanoparticle can, in various aspects, be present in a heterojuction cell in one or more of these devices.

In one aspect, the device can comprise a solar cell. A solar cell is a device that converts solar energy into electricity through the photovoltaic effect. The term "solar cell" is generally intended to refer to devices that capture energy from sunlight, while the term "photovoltaic cell" is used when the source is unspecified. During the functioning of a photovoltaic device, a disclosed nanoparticle can absorb light, giving rise to excited states (i.e., hole and electron separation). The holes or electrons can then diffuse to, for example, a surface of the nanoparticle. In order to generate electricity, these charge carriers can travel from nanoparticle to nanoparticle (in the case of electrons) and then to the polymer and electrodes, and thereby generating an electrical current.

A disclosed embodiment can be used in combination with any solar cell. Methods of making solar cells and the components thereof are well known in the art. A solar cell generally comprises a photovoltaic cell, in which a disclosed material could be incorporated therein. A solar cell can also comprise a photovoltaic module, wherein photovoltaic cells can be connected in series and/or parallel to form an array of modules, thus increasing total available power output.

In one aspect, the solar cell can comprise a heterojunction solar cell. In such devices, rather than having two bulk materials pressed against each other where one is more likely to become p-doped and the other is more likely to become n-doped (a bulk junction cell), the two materials can be, in one aspect, contacted and/or blended together. Typically, one of these materials can act as a hole conductor, and the other material can act as an electron conductor. In a specific aspect, one or both of these materials can absorb light in the visible region of the spectrum. In such aspects, the materials can then be combined together to create a heterojunction cell.

It should be appreciated that at present, one barrier to the efficiency of heterojunction in solar cells is related to the junction between the two materials (i.e., the heterojunction). The common method of fabricating devices from such blends is to mix the nanoparticles and conducting polymers together and to deposit the resulting blend on a substrate. However, materials made by such methods exhibit some significant challenges. Thus, as will be apparent, the present disclosure can, in one aspect, at least partially obviate this challenge. The disclosed results demonstrate that the use of a disclosed embodiment in a solar cell can, in some aspects, even enable the cell to capture the majority of the UV-visible and near infrared spectrum.

In a further aspect, the device can comprise a sensor. In sensors, for example, rather than absorbing sunlight to generate electricity, a device can be adapted to absorb, for example, gamma radiation, or electromagnetic radiation over some other desired portion of the electromagnetic spectrum.

This would again result in electron transfer and an excited state. However, instead of generating electricity, such a device can be equipped with a detection scheme adapted to sense any change in the resistance of the conducting polymer.

In still a further aspect, the device can comprise an electrode, such as an oxygen reduction electrode, or a device comprising the same. In such a device, the nanoparticle can comprise a metal suitable for use in reducing oxygen. In another aspect, the device can comprise a fuel cell.

It is understood that the devices can be used in combination with the disclosed compounds, oligomers, polymers, copolymers, nanoparticles, polymer-nanoparticle compositions, and methods.

F. Methods

In one aspect, a disclosed method for producing a polymer nanoparticle composition comprises: (a) providing a film comprising an at least partially electrically conductive oligomer, polymer, or copolymer comprising a plurality of metal complex residues having at least one metal center therein; and (b) growing at least one nanoparticle from the at least one metal center; thereby producing the polymer-nanoparticle composition.

In one aspect, the at least partially electrically conductive copolymer comprises both a plurality of metal complex residues having at least one metal center therein; and a plurality of residues not having metal complexes therein.

In one aspect, the step of providing the film comprising an at least partially electrically conductive oligomer, polymer, or copolymer comprises: (a) providing a first monomer deposited onto at least a portion of a substrate; and (b) polymerizing the first monomer; thereby providing the film. Any suitable polymerization technique can be used and the present invention is not intended to be limited to any particular technique. For example, the first monomer can be electropolymerized. Any method of polymerization to produce a disclosed polymer is contemplated for use, including but not limited to, methods of polymerization comprising cationic, anionic, condensation, metathesis, and/or radical polymer growth.

In a further aspect, the step of providing the film comprising an at least partially electrically conductive oligomer, polymer, or copolymer comprises: providing a second monomer deposited onto at least a portion of a substrate; and copolymerizing the first monomer and the second monomer, thereby providing the film. The ratio of the first and second monomer can be any appropriate ratio. For example, the molar ratio of the first monomer to the second monomer can from about 1:1 to about 1:100, from about 1:25 to about 1:100, or from about 1:50 to about 1:100.

It should be appreciated that a further advantage of the methods disclosed herein relates to the ease of processing that they afford. In particular, a monomer can be directly deposited onto a substrate and either polymerized first followed optionally by the growth of the nanoparticle directly in the polymer film, or polymerized after the growth of the nanoparticle in the monomer matrix itself.

Figure 11:
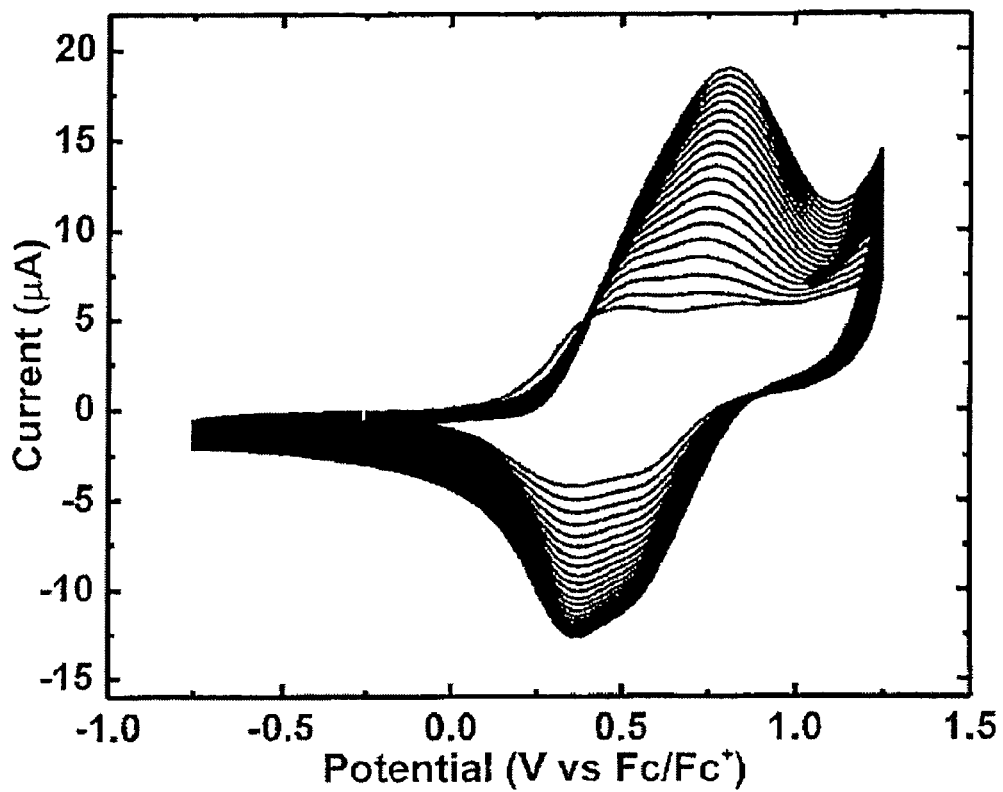
FIG. 11 is a cyclic voltammogram illustrating the electrodeposition of polymeric films made from the monomer of FIG. 1.
Figure 12:
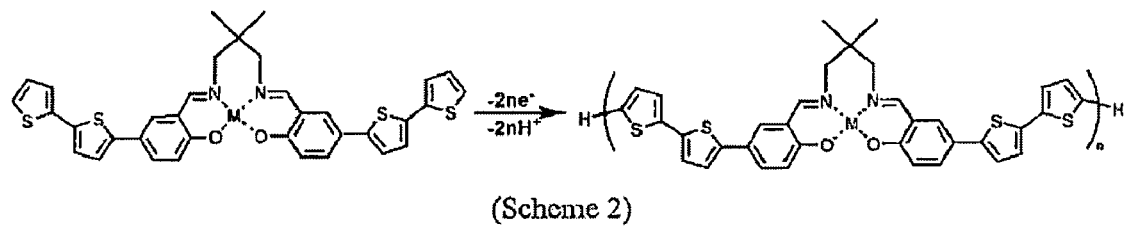
FIG. 12 is an illustration of the electrochemically induced polymerization of one particular species of the class of monomers depicted in FIG. 1.

As an example, FIG. 11 is a cyclic voltammogram which illustrates the means by which films of the compound of FIG. 1 can be made. In contrast to existing technologies in which films are made from nanoparticle/conductive polymer compositions by drop-casting or spin-coating them onto a surface, the present films can be made by, for example, electrodeposition, thus providing better control of the film thickness and uniformity. Such an exemplary process utilizes a potentiostat to electrochemically polymerize the materials through the generation of a radical cation originating from the monomer, followed by radical-to-radical coupling as shown in FIG. 12.

The graph in FIG. 11 shows the electrochemistry and the growth of the film on an electrode. One advantage of this process is that, unlike many known processes, there is no separate film making step. Rather, the film is formed during the polymerization process itself.

Figure 13:
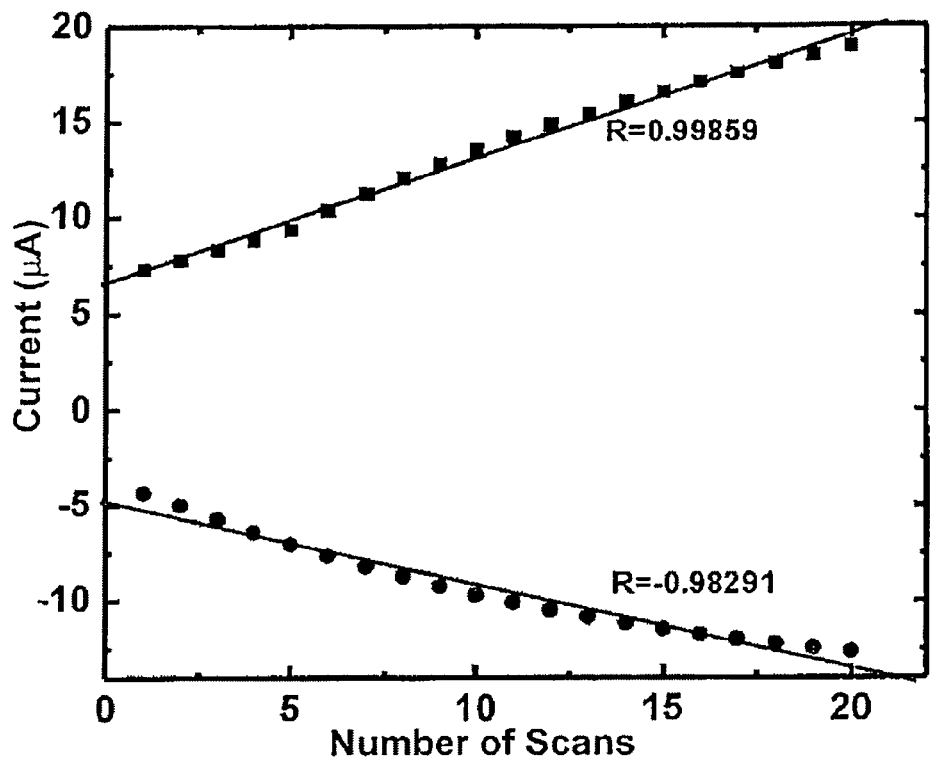
FIG. 13 is a graph summarizing the data of FIG. 11.

With reference to FIG. 11, as the polymers are grown, they can be bound to an electrode. Hence, each subsequent scan, for example, starting at −0.5 volts and going oxidatively to +1.5 volts with respect to a silver/silver nitrate reference electrode (and subsequently returning to 0 volts) can require more current than the previous scan, since the constantly growing film must be charged before any electrochemistry can occur. The chart of FIG. 13 depicts the amount of current that can be passed through an exemplary film as a function of the number of scans, and hence indicates the linearity of the growth of the exemplary polymerized film. It will be appreciated from the chart of FIG. 13 that, in optimizing a device, if it is determined that a particular film thickness gives optimal results, the number of scans can be calibrated to this thickness. This, in turn, can determine the amount of current that can be passed, and allow a film having a desired thickness to be reproducibly achieved by empirically deriving this amount of current.

Figure 14:
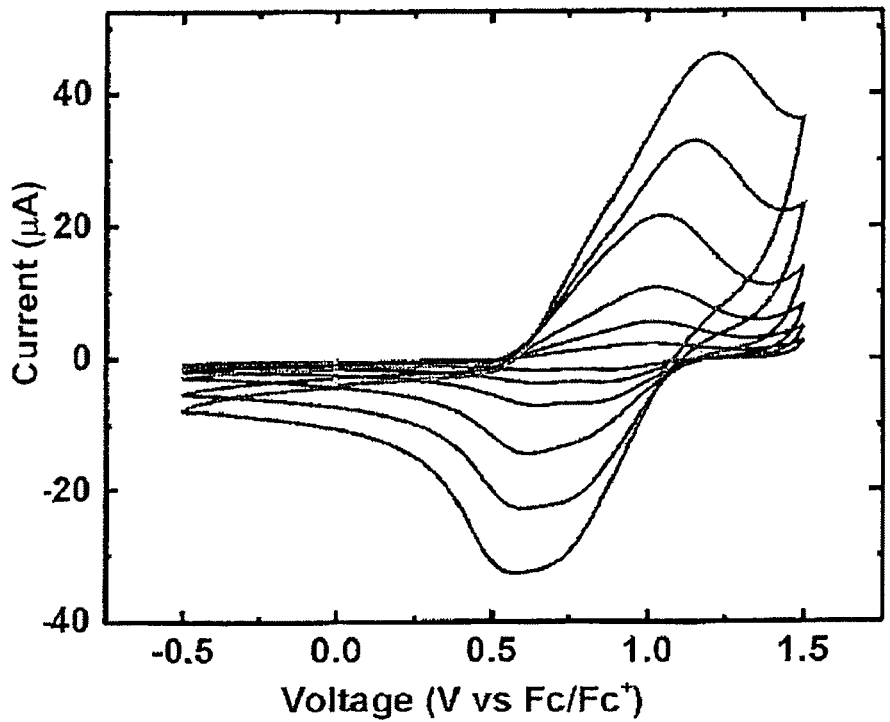
FIG. 14 is a graph depicting the characterization of a film formed by the polymerization shown in FIG. 12, in which the film on the electrode is characterized by running it through a cyclical voltammogram at different scan rates ranging from a slow scan rate (10 mV/s) to a fast scan rate (500 mV/s)
Figure 15:
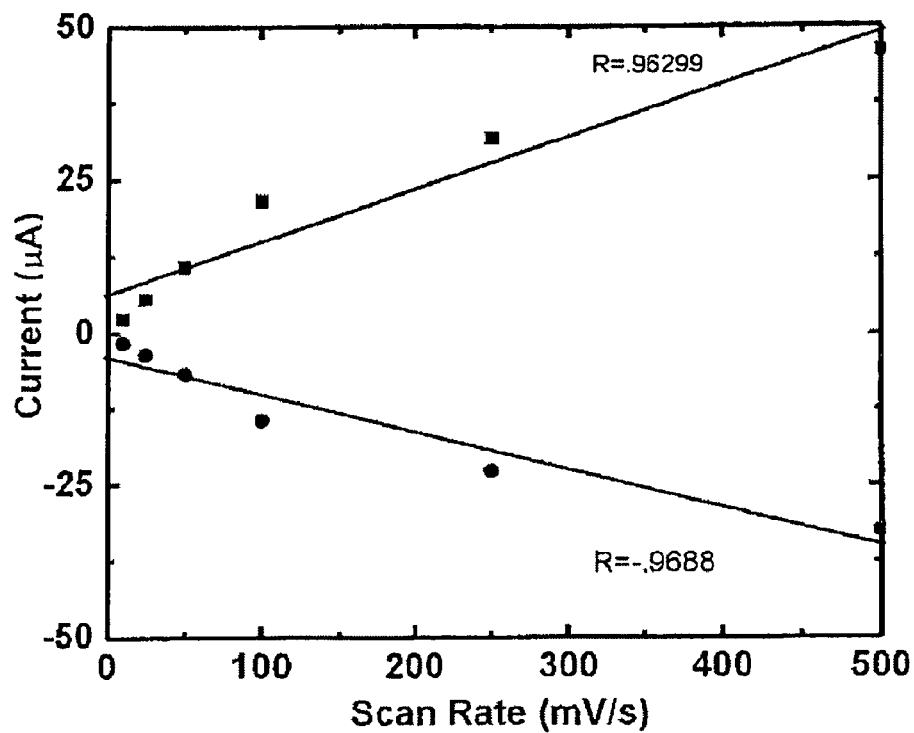
FIG. 15 is a graph summarizing the data of FIG. 14.
Figure 16:
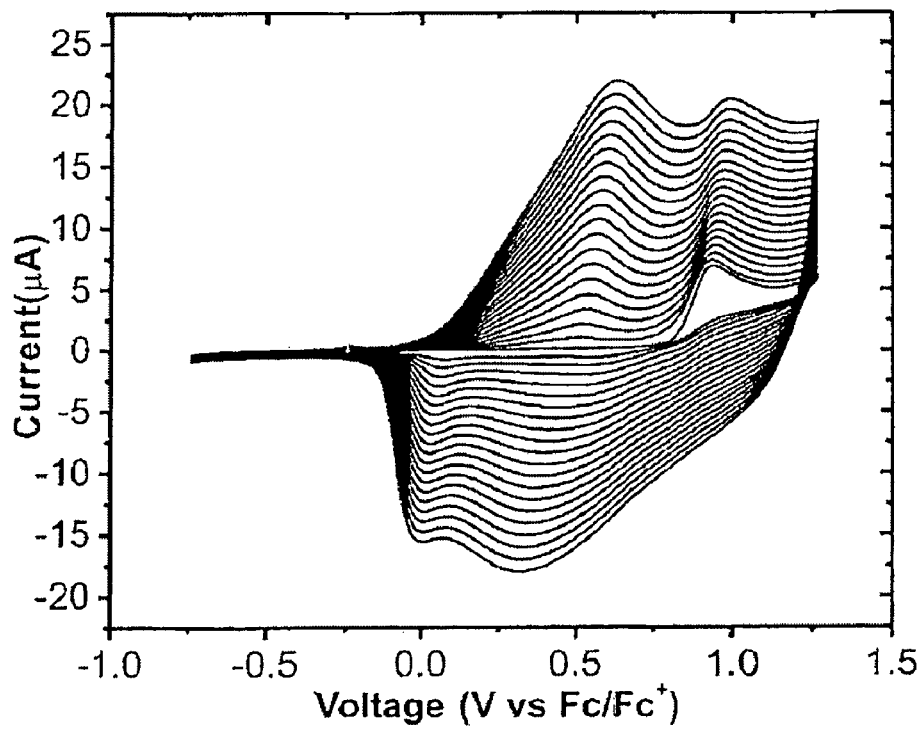
FIG. 16 is a cyclic voltammogram illustrating the electrodeposition of a copolymer formed by the electrochemical process depicted in FIG. 18.

FIG. 14 shown the results of exemplary studies carried out on films formed by the various aspects of the present invention. In one aspect, the film can be thoroughly rinsed to prevent any further polymerization, and can be put in a clean solution which can be devoid of monomer. In another aspect, the film on the electrode can then be characterized by cyclic voltammetry at varying scan rates. For example, the first scanning cycle can be at about 10 mV/s (slow), and the last scanning cycle can be at about 500 mV/s (fast). The resulting data can be plotted as in FIG. 15. The maximum scan rate that can be achieved without departing from linearity can thus provides an indication of how well the film openly accepts, and then recovers from, changes in redox state. As shown in FIG. 15, the exemplary data remained substantially linear to the maximum scan rate, indicating that the materials can diffuse in and out of the film without significant difficulty (i.e., the film is fairly porous), so that growth of nanoparticles can readily occur.

Figure 17:
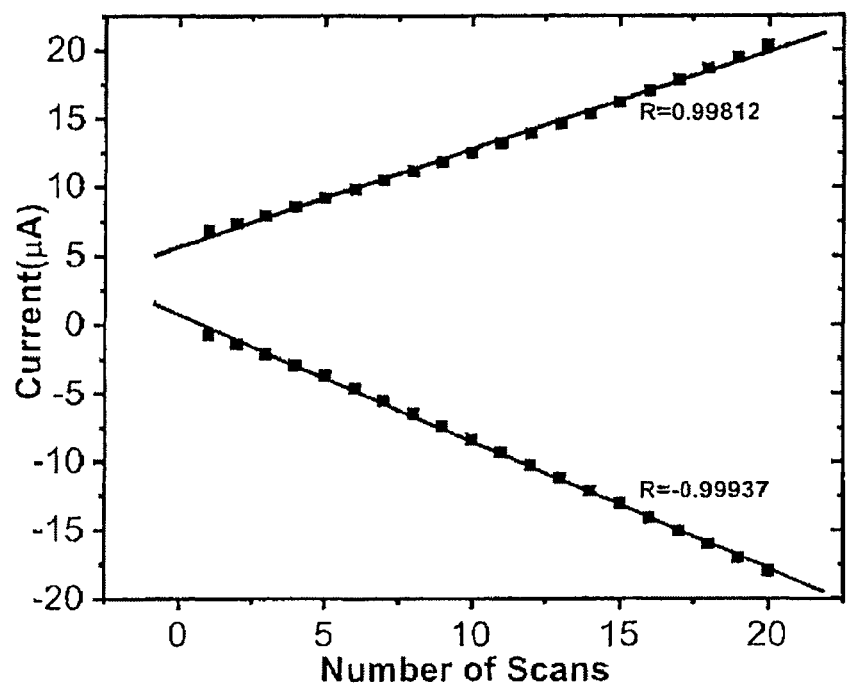
FIG. 17 is a graph summarizing the data of FIG. 16.
Figure 20:
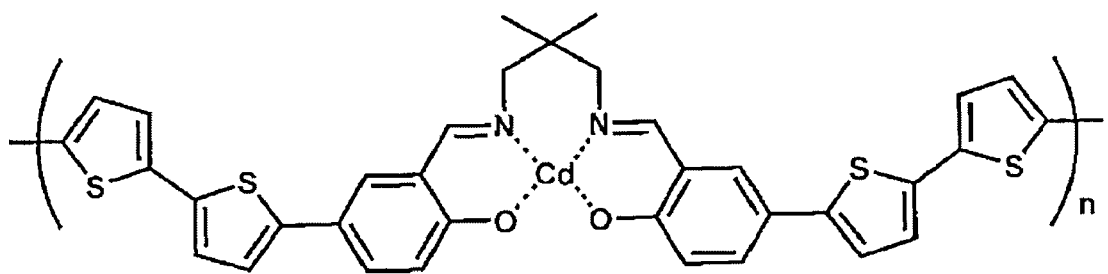
FIG. 20 is an illustration of the chemical structure of the polymer formed by the electrochemical process of FIG. 12.
Figure 21:
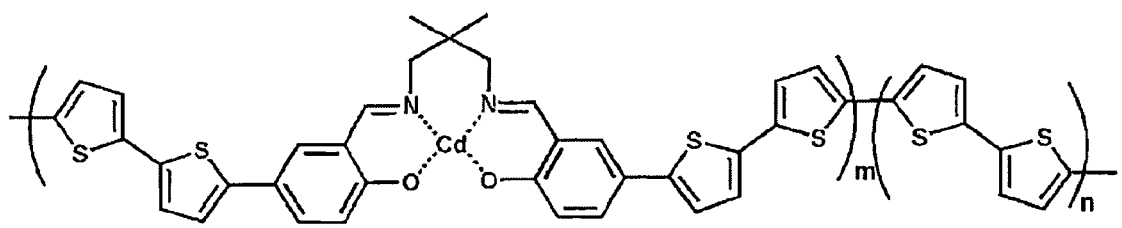
FIG. 21 is an illustration of the chemical structure of the copolymer formed by the electrochemical process depicted in FIG. 18.

FIGS. 16-19 depict the corresponding data obtained when a monomer, such as that illustrated in FIG. 20, is diluted with bithiophene to a ratio of about 50:1 bithiophene to monomer. In the resulting copolymer (depicted in FIG. 21), the metal seed points are spread out in the film. In FIG. 17, a linear dependence between the current and the number of scans can be observed, indicating formation of the film and control of film thickness.

Figure 22:
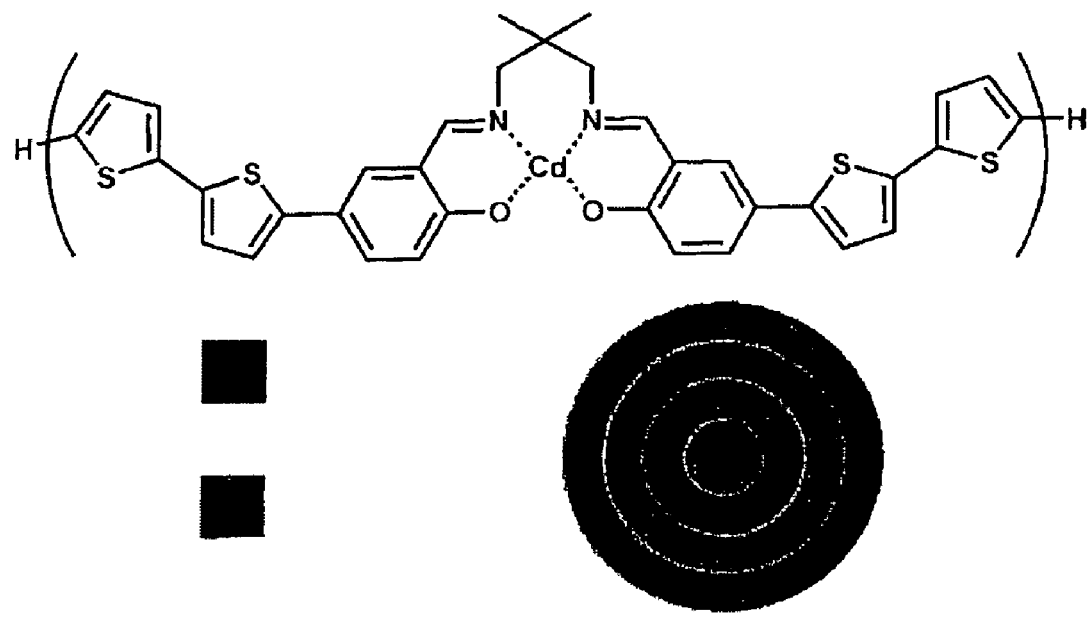
FIG. 22 is an illustration of the layer by layer growth of cadmium sulfide nanoparticles on the metal centers of the polymer of FIG. 20.

FIG. 22 summarizes the growth process of nanoparticles with the previously described polymer film. The growth occurs in a step-wise growth process in which the polymer, such as, for example, with cadmium built into it, is exposed to a saturated solution of, for example, $H_2S$ and methylene chloride, surrounding the cadmium atoms built into the polymer with sulfides. The exemplary polymer can then be rinsed with solvent and then exposed to a solution containing $Cd^{2+}$ ions. The process can then be repeated. This process of iteratively treating the polymer in this manner thus generates semiconductor nanoparticles on or within the polymer matrix.

Figure 23:
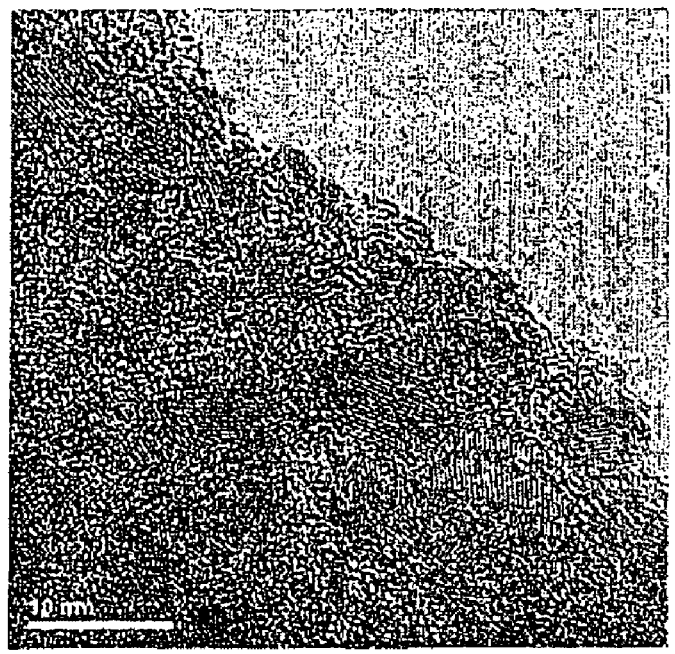
FIG. 23 is a transmission electron micrograph of a film of the polymer after the growth of nanoparticles shown in FIG. 9.
Figure 24:
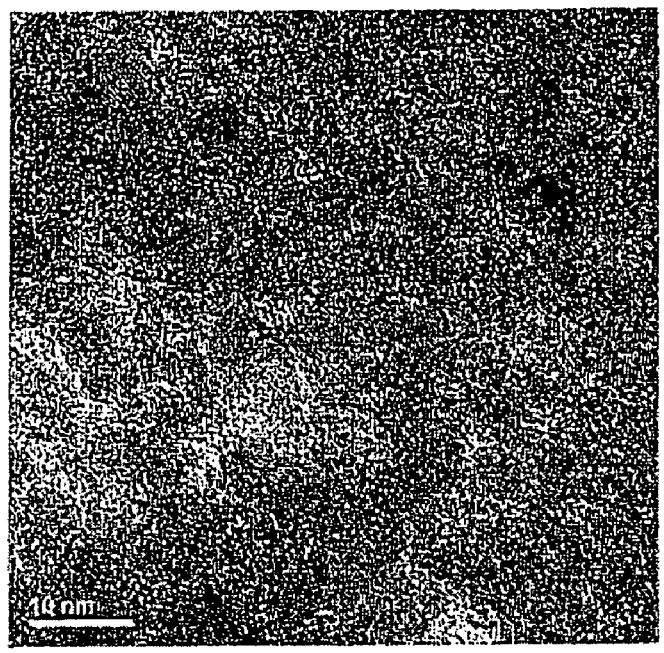
FIG. 24 is a micrograph of a film of the polymer after the growth of nanoparticles shown in FIG. 10.

The nanoparticles represented in FIG. 22, for example, can also be characterized by TEM (tunneling electron microscopy), as illustrated in FIGS. 23 and 24 (the first TEM was obtained after 2 Cd/S cycles, while the second TEM was obtained after 4 Cd/S cycles). These micrographs illustrate the conductive polymer layer. The dark spots on the image are cadmium sulfide semiconductor material. Close examination of these micrographs reveals that the material is a semiconductor crystal with crystalline fringes. Characterization of the semiconductor material by X-ray diffraction in the TEM has revealed that the elemental composition of the material comprises cadmium and sulfur.

Figure 25:
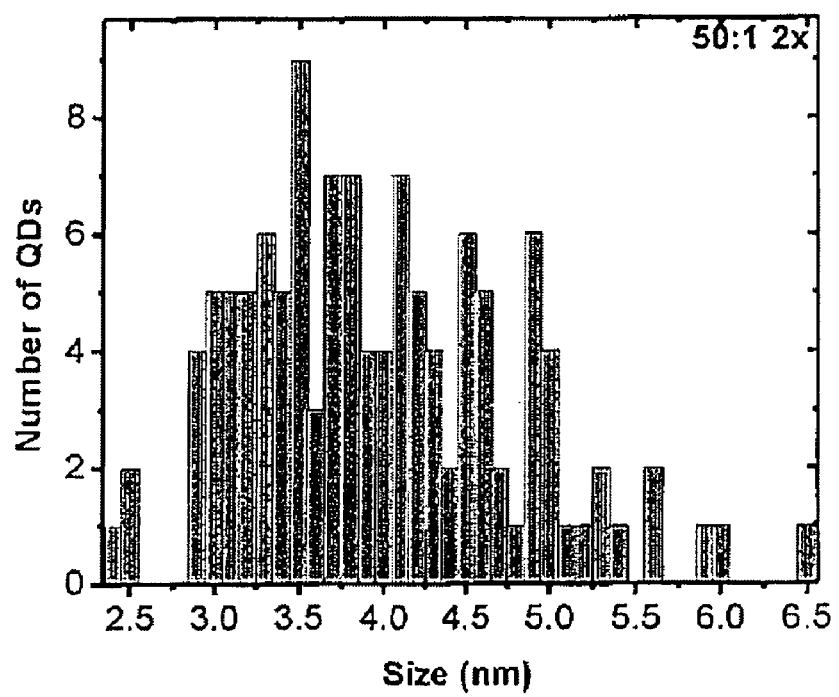
FIG. 25 is a graph of the size distribution of nanoparticles formed after two cycles of the process depicted in FIG. 22, but using the bithiophene copolymer depicted in FIG. 21.
Figure 26:
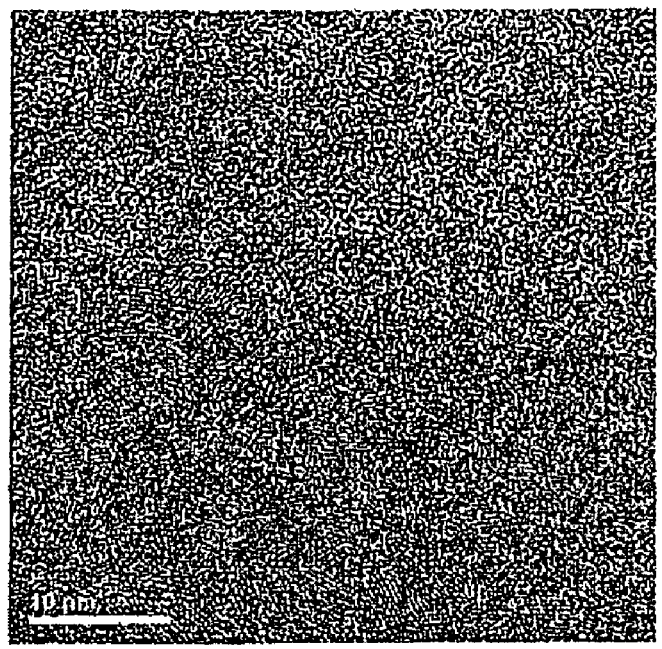
FIG. 26 is a micrograph of a film of the polymer after the growth of nanoparticles shown in FIG. 25.
Figure 27:
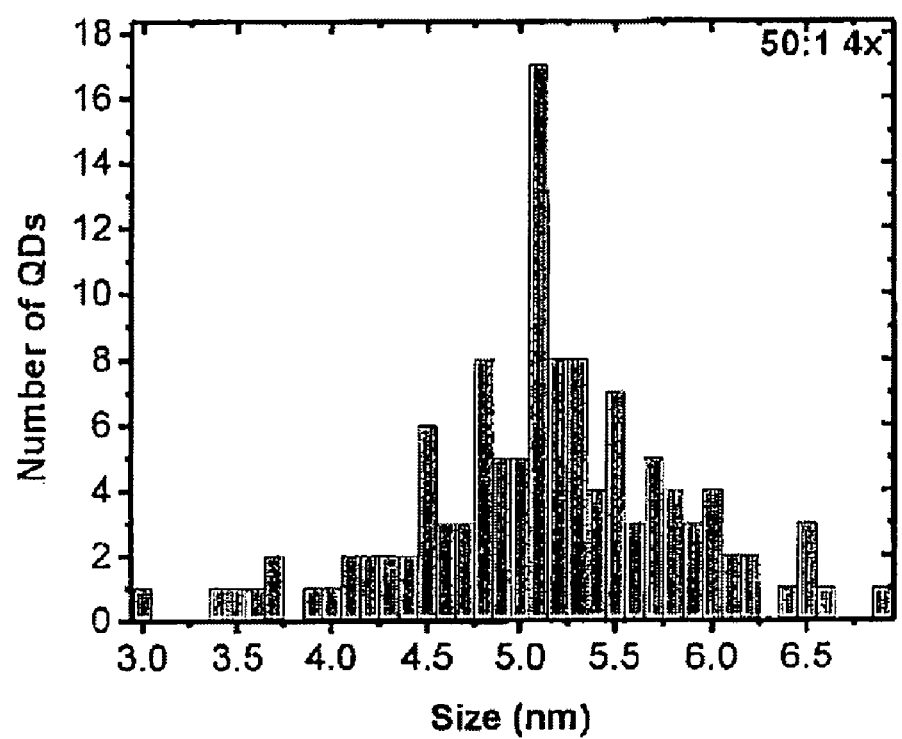
FIG. 27 is a graph of the size distribution of nanoparticles formed after four cycles of the process depicted in FIG. 22, but using the bithiophene copolymer depicted in FIG. 21.

FIGS. 25-28 show the corresponding results obtained with the 50:1 bithiophene/monomer copolymer. As shown by the two TEMs (the first obtained after 2 Cd/S cycles, the second obtained after 4 Cd/S cycles), the nanoparticles are more spread out and there are less of them in the film per unit volume or area, as would be expected due to the dilution of the metal-containing monomer. Analogous results to the previous example can be obtained for size distribution, as illustrated in the charts of FIG. 25 and FIG. 27.

G. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Materials and General Methods

The following chemicals were used as received: 5-bromo-salkyladehyde (Alfa Aesar), 2,2'-bithiophene (Aldrich), tributyltin chloride (Alfa Aesar), 2,2-dimethyl-1,3-propanediamine (TCI), 1,2-phenylenediamine (TCI), 2,2'-ethylenedioxybis(ethylamine) (Aldrich). All solvents were dried using an Innovative Technology, Pure Solv solvent purifier with a double purifying column. All reactions were performed using standard Schlenk techniques. NMR spectra were obtained using Varian Unity+300. TEM pictures were taken using a JEOL 2010F microscope. Samples were prepared on gold grids with a carbon support film purchased from Electron Microscopy Sciences.

All electrochemistry was performed using an Autolab Potentiostat. Experiments were run in 0.1 M tetrabutylammonium hexafluorophosphate in methylene chloride. A non-aqueous reference electrode of 0.1 M silver nitrate in acetonitrile was used. A platinum button was used as the working electrode and a platinum coil was used as the counter electrode. XPS samples were prepared on 0.002" thick Stainless Steel.

2. Quantum Dot Growth

Polymerized films were treated with subsequent solutions of metal salts ($MNO_3$) and a saturated solution of hydrogen sulfide ($H_2S$).

3. Synthesis of 5-(2,2'-bithiophene-5-yl)-2-hydroxybenzaldehyde (1)

To a mixture of 5-bromosalkylaldehyde (3.5 g, 17.4 mmol), and $Pd(PPh_3)_2Cl_2$ (0.613 g, 0.88 mmol) in 40 mL of dry toluene was added 2-(tributylstannyl)bithiophene (9.56 g, 21 mmol). The reaction mixture was heated to 80° C. for 48 h under argon. The reaction was cooled and dried in vacuo to give a yellow solid. The solid was dissolved in $CH_2Cl_2$, then filtered through a silica plug. The filtrate was washed with dilute $NH_4Cl$ and the organic phase was dried over $MgSO_4$. Solvent was removed in vacuo to give a yellow solid that was then washed with hexanes. The yellow solid was recrystallized from $CH_2Cl_2$ and hexanes, then dried in vacuo to give the product (3.96 g, 79%).

4. Synthesis of N,N'-((2,2'-dimethyl)propyl)bis(5-(2,2'-bithiophene-5-yl) salcylidenimine (2A)

To a solution of 1 (1.00 g, 3.49 mmol) dissolved in $CH_2Cl_2$ (200 mL) was added EtOH (200 mL), and 1,3-diamino-2,2'-dimethylpropane (0.1784 g, 1.75 mmol). The reaction mixture was stirred at room temperature for 8 hours, and then $CH_2Cl_2$ was removed in vacuo. The reaction mixture was filtered to give an orange solid that was then dried in vacuo to give the product (0.954 g, 86%).

5. Synthesis of N,N'-(2,2'-(ethylenedioxy)bis(ethyl))bis(5-(2,2'-bithiophene-5-yl)salcylidenimine (2B)

To a solution of 1 (1.00 g, 3.49 mmol) dissolved in $CH_2Cl_2$ (200 mL) was added EtOH (200 mL), and 2,2'-(ethylene dioxy)-bis(ethylamine) (0.282 mL, 1.75 mmol). The reaction mixture was stirred at room temperature for 8 hours, and then $CH_2Cl_2$ was removed in vacuo. The reaction mixture was filtered to give an orange solid that was then dried in vacuo to give the product (0.900 g, 80%).

6. Synthesis of N,N'-phenylenebis(5-(2,2'-bithiophene-5-yl)salcylidenimine (2C)

To a solution of 1 (1.00 g, 3.49 mmol) dissolved in $CH_2Cl_2$ (200 mL) was added EtOH (200 mL), and 1,2-phenylenediamine (0.188 g, 1.75 mmol). The reaction mixture was stirred at room temperature for 8 hours, and then $CH_2Cl_2$ was removed in vacuo. The reaction mixture was filtered to give an brown solid that was then dried in vacuo to give the product (1.02 g, 85%).

7. Synthesis of N,N'-((2,2'-dimethyl)propyl)bis(5-(2, 2'bithiophene-5-yl) salcylideniminatocadmium(II) (3(M=Cd))

To a solution of 2a-c (130 mg, 0.2 mmol) in 30 mL of $CH_2Cl_2$ was added a solution of NaH (10 mg) in MeOH (15 mL). $Cd(OAc)2.2H_2O$ was dissolved in MeOH (15 mL) then added to the reaction mixture. The reaction was heated to 50° C. and left to stir for 8 h. The $CH_2Cl_2$ was removed in vacuo and the resulting precipitate was collected to give 3 (M=Cd).

8. Polymer Films

In one aspect, a monomer was electropolymerized as according to Scheme 2 (see FIG. 12) to give electrode confined thin films. The resulting conducting metallopolymer films were characterized by electrochemistry, UV-vis spectroscopy, XPS, and UV-vis spectroelectrochemistry. Representative XPS data for poly-3 (M=Cd) is shown in Table 1.

TABLE 1

XPS of electropolymerized 3 (M = Cd):bithiophene on stainless steel. Theoretical values are shown in parantheses.

|      | Monomer | 1:1 | 1:25 | 1:50 | 1:100 |
|------|---------|-----|------|------|-------|
| Cd:S | 1:2.56 (1:4) | 1:4 (1:2.66) | 1:8 (1:19) | 1:21 (1:36) | 1:125 (1:69) |

Figure 18:
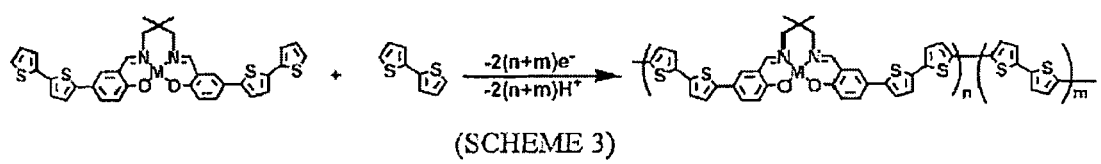
FIG. 18 is an illustration of the electrochemically induced copolymerization of bithiophene and a particular species of the class of monomers depicted in FIG. 1.
Figure 19:
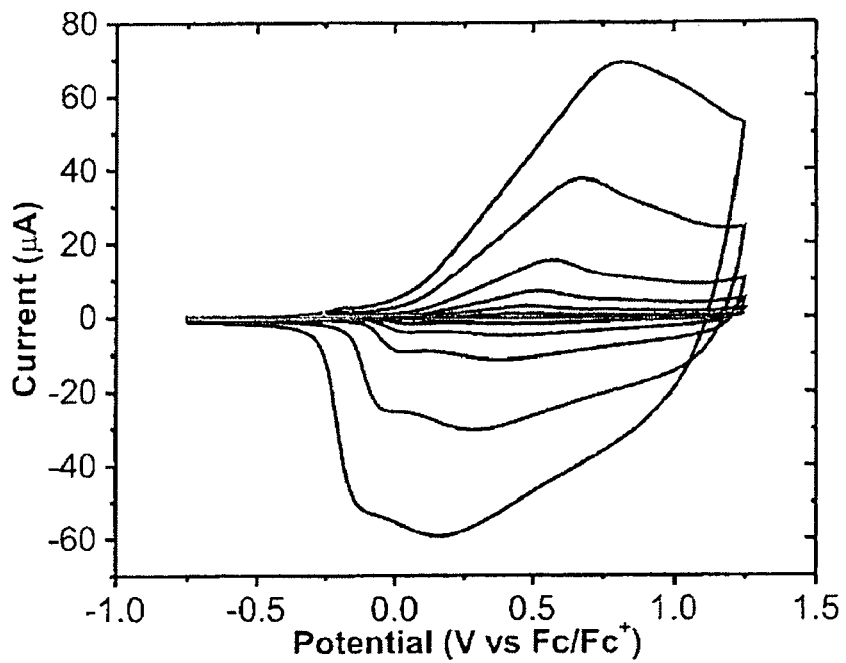
FIG. 19 is a graph depicting the characterization of a film formed by the polymerization shown in FIG. 18, in which the film on the electrode is characterized by running it through a cyclical voltammogram at different scan rates ranging from a slow scan rate (10 mV/s) to a fast scan rate (500 mV/s)

In addition to the homopolymers, a series of random alternating copolymers have been synthesized and characterized according to Scheme 3 (see FIG. 18). These copolymers incorporate differing amounts of bithiophene in order to vary the spacing and films. Films were prepared by electropolymerization of stock solutions that contained the following ratios of metal complex:bithiophene: 1:1, 1:25, 1:50, and 1:100. Although it is not a direct dependence, as the ratio of monomer to bithiophene is increased, there is an increase in the Cd:S ratio in the resulting films.

Figure 29:
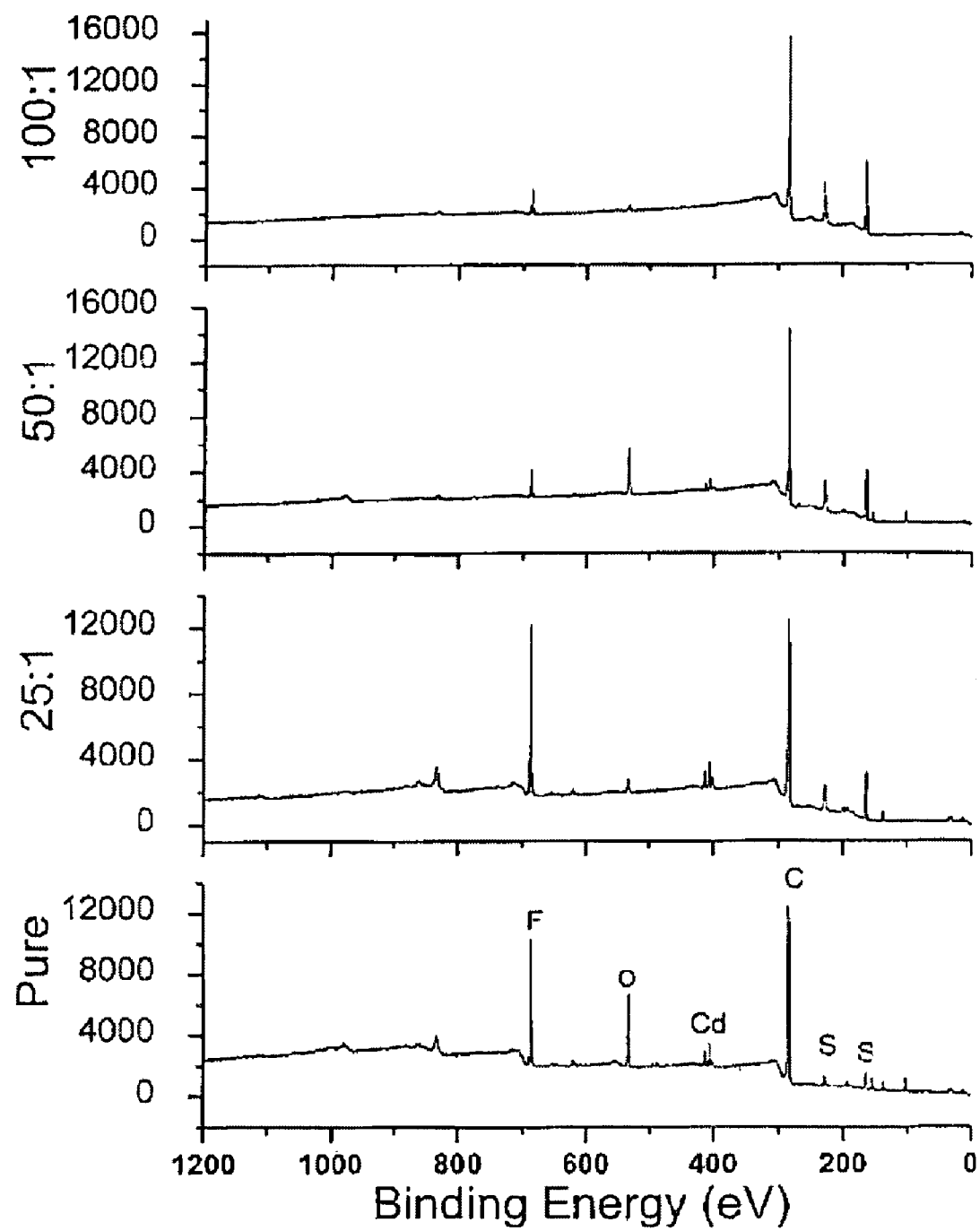
FIG. 29 is a series of XPS spectra on the polymer of FIG. 20 (the undiluted cadmium-containing monomer) and copolymers of the type shown in FIG. 31 made with successively greater ratios of bithiophene to the cadmium monomer.
Figure 30:
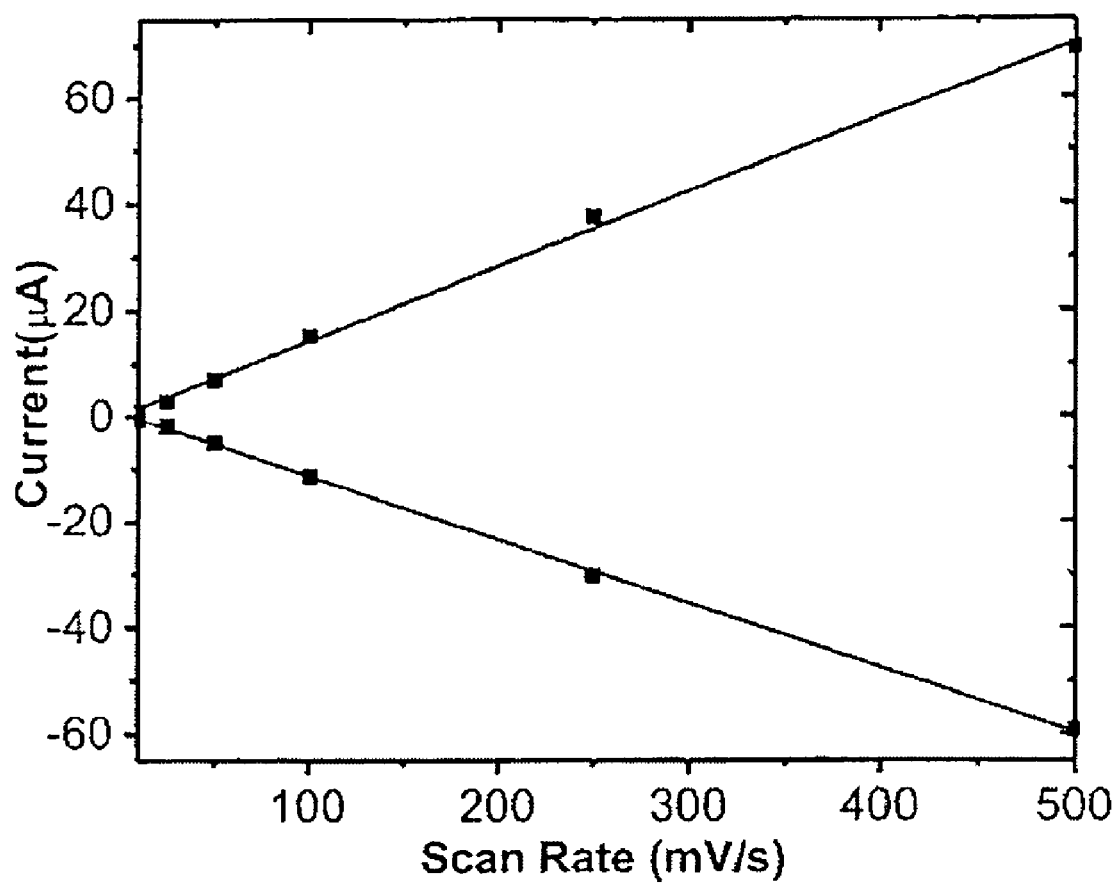
FIG. 30 is a graph summarizing the data of FIG. 19.

FIG. 29 depicts exemplary XPS spectra, beginning with the spectrum obtained on a pure (undiluted) cadmium containing monomer (bottom) and continuing through successive dilutions of the monomer with bithiophene up to a ratio of 100:1 of bithiophene to monomer (top). Notably, in the undiluted material, the cadmium and sulfur peaks are clearly visible. As dilution progresses, however, the cadmium peak becomes increasingly difficult to discern, thus demonstrating the dilution of the metal seed points. On the other hand, the sulfur peaks become increasingly more prominent, thus reflecting the increasing concentration of bithiophene in the material. Thus, the present invention can provide the ability to tailor the dilution of and/or distribution of seed points.

3. Polymer-Nanoparticle Compositions

Figure 28:
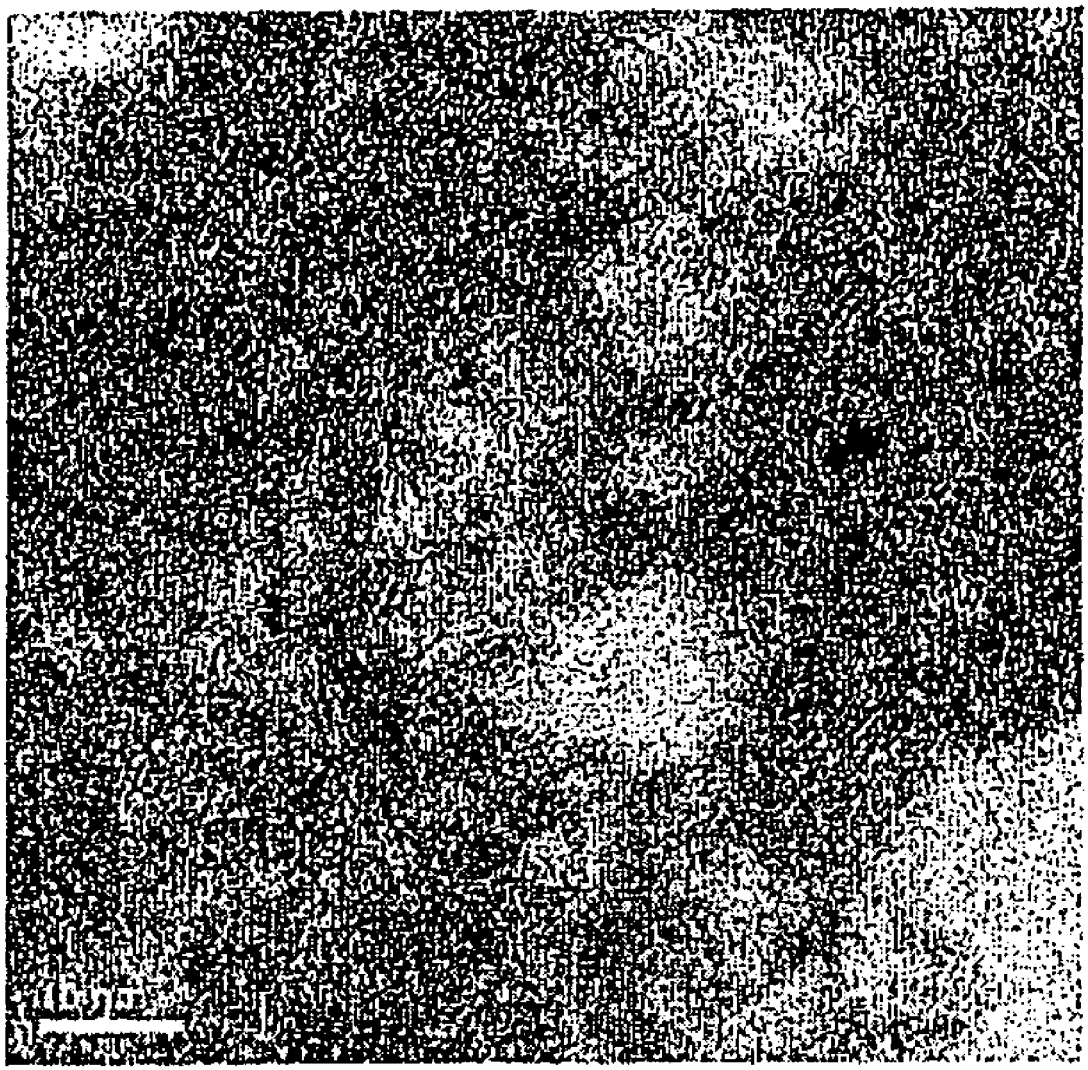
FIG. 28 is a micrograph of a film of the polymer after the growth of nanoparticles shown in FIG. 27.

Semiconductor nanoparticles were grown directly within polymerized films by exposing the films sequentially to a source of sufide ($H_2S$) and metal ions ($Cd^{2+}$, $Ga^{3+}$, $Cu^{2+}$, or $Pb^{2+}$). This step-wise growth process allows control over the nanoparticle size and terminating surface. FIG. 28 shows the presence of 3-4 nm semiconductor nanoparticles that were grown directly in the conducting metallopolymer matrix via this process as observed by TEM.

Hybrid materials comprising nanoparticles of other materials attached to conducting polymer matrix have been prepared using methods similar to those described above for CdS. These include, but are not limited to, particles of Pd, CdSe, CdTe, $Ga_2S_3$, $Ga_2Se_3$, $Ga_2Te_3$, $CuGaS_2$, $CuGaSe_2$, PbS, PbSe, $CuInS_2$, or $CuInSe_2$.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A polymer-nanoparticle composition comprising:
   a film comprising an at least partially electrically conductive oligomer, polymer, or copolymer; and at least one nanoparticle at least partially disposed therein;
   wherein the at least partially electrically conductive oligomer, polymer, or copolymer is in electrical communication with the nanoparticle, and wherein the at least one nanoparticle is bonded to at least one metal center present in a metal complex residue in the at least partially electrically conductive oligomer, polymer, or copolymer by means of a covalent and/or ionic bond.

2. The polymer-nanoparticle composition of claim 1, wherein the at least one nanoparticle is at least partially semiconducting.

3. The polymer-nanoparticle composition of claim 1, wherein the at least one nanoparticle comprises a transition metal, an inert metal, a catalytic metal, a platinum group metal, or an alloy or combination thereof.

4. The polymer-nanoparticle composition of claim 1, wherein the at least one nanoparticle is grown from at least one metal center in a metal complex residue in the at least partially electrically conductive oligomer, polymer, or copolymer.

5. The polymer-nanoparticle composition of claim 1, wherein the at least partially electrically conductive oligomer, polymer, or copolymer comprises a residue represented by a formula:

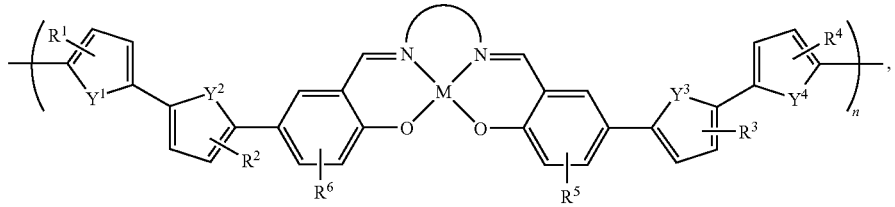

wherein n is an integer from 1 to 100,000;
wherein each $Y^1$, $Y^2$, $Y^3$, and $Y^4$ is independently selected from O, S, and NH;
wherein M is a metal;
wherein each $R^1$ and $R^4$ independently comprises 2 substituents independently selected from hydrogen and optionally substituted organic residue comprising from 1 to 12 carbons;
wherein each $R^2$ and $R^3$ independently comprises 3 substituents independently selected from hydrogen and optionally substituted organic residue comprising from 1 to 12 carbons;
wherein each $R^5$ and $R^6$ independently comprises from 1 to 3 substituents independently selected from hydrogen and optionally substituted organic residue comprising from 1 to 12 carbons;
wherein the general structural residue

represents a ligand selected from optionally substituted heteroalkyl, optionally substituted heterocycloalkyl, and optionally substituted heteroaryl; and wherein the at least one nanoparticle is grown therefrom.

6. The composition of claim 1, wherein the nanoparticle comprises Cd, Pb, Ga, Cu, or an alloy or combination thereof.

* * * * *